(12) United States Patent
Baillie et al.

(10) Patent No.: US 10,406,099 B2
(45) Date of Patent: *Sep. 10, 2019

(54) BIOERODIBLE CONTRACEPTIVE IMPLANT AND METHODS OF USE THEREOF

(71) Applicant: Gesea Biosciences Inc., Lynnwood, WA (US)

(72) Inventors: John H. Baillie, Glen Ellen, CA (US); Ruth Baillie, Glen Ellen, WA (US); George Blouin, Lynnwood, WA (US); Newsha Farahani, Issaquah, WA (US); Christopher Marx, Mukilteo, WA (US)

(73) Assignee: GESEA BIOSCIENCES, INC., San Luis Obispo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/961,733

(22) Filed: Apr. 24, 2018

(65) Prior Publication Data

US 2018/0303659 A1 Oct. 25, 2018

Related U.S. Application Data

(63) Continuation of application No. 15/720,845, filed on Sep. 29, 2017, now Pat. No. 9,980,850.

(Continued)

(51) Int. Cl.
*A61K 9/00* (2006.01)
*A61F 6/08* (2006.01)
(Continued)

(52) U.S. Cl.
CPC ............ *A61K 9/0024* (2013.01); *A61F 6/08* (2013.01); *A61F 6/22* (2013.01); *A61K 9/0002* (2013.01);
(Continued)

(58) Field of Classification Search
None
See application file for complete search history.

(56) References Cited

U.S. PATENT DOCUMENTS 4,957,119 A 9/1990 De Nijs
5,035,891 A 7/1991 Runkel et al.
(Continued)

FOREIGN PATENT DOCUMENTS

WO 1990/010437 A1 9/1990

OTHER PUBLICATIONS

Raymond et al. (Contraceptive efficacy, pharmacokinetics, and safety of Annuelle biodegradable norethindrone pellet implants, Fertility and Sterility (1996), 66(6):954-961. (Year: 1996).*

(Continued)

*Primary Examiner* — Robert A Wax
*Assistant Examiner* — Melissa S Mercier
(74) *Attorney, Agent, or Firm* — Dianne E. Reed; VLP Law Group, LLP

(57) ABSTRACT

A contraceptive drug delivery system is provided in the form of a controlled release, bioerodible pellet for subdermal implantation. The pellet is bioerodible, and provides for the sustained release of a contraceptive agent over an extended time period. Bioerosion products are water soluble, bioresorbed, or both, obviating the need for surgical removal of the implant. Methods of using the drug delivery system, including in female contraception, are also provided.

24 Claims, 14 Drawing Sheets

Related U.S. Application Data

(60) Provisional application No. 62/401,167, filed on Sep. 29, 2016.

(51) Int. Cl.

| | | |
|---|---|---|
| *A61F 6/22* | (2006.01) | |
| *A61K 31/167* | (2006.01) | |
| *A61K 31/192* | (2006.01) | |
| *A61K 31/325* | (2006.01) | |
| *A61K 31/57* | (2006.01) | |
| *A61K 31/593* | (2006.01) | |
| *A61K 47/10* | (2017.01) | |
| *A61K 47/12* | (2006.01) | |
| *A61K 47/24* | (2006.01) | |
| *A61K 47/28* | (2006.01) | |
| *A61K 31/567* | (2006.01) | |
| *A61K 47/36* | (2006.01) | |
| *A61K 9/50* | (2006.01) | |
| *A61F 2/30* | (2006.01) | |
| *A61L 27/54* | (2006.01) | |
| *A61L 27/58* | (2006.01) | |

(52) U.S. Cl.
CPC .......... *A61K 9/5021* (2013.01); *A61K 31/167* (2013.01); *A61K 31/192* (2013.01); *A61K 31/325* (2013.01); *A61K 31/567* (2013.01); *A61K 31/57* (2013.01); *A61K 31/593* (2013.01); *A61K 47/10* (2013.01); *A61K 47/12* (2013.01); *A61K 47/24* (2013.01); *A61K 47/28* (2013.01); *A61K 47/36* (2013.01); *A61F 2002/30677* (2013.01); *A61L 27/54* (2013.01); *A61L 27/58* (2013.01); *A61L 2300/404* (2013.01)

(56) References Cited

U.S. PATENT DOCUMENTS

| | | |
|---|---|---|
| 5,039,660 A | 8/1991 | Leonard et al. |
| 5,069,909 A | 12/1991 | Sharma et al. |
| 5,137,669 A | 8/1992 | Leonard et al. |
| 5,543,156 A | 8/1996 | Roorda et al. |
| 5,660,848 A | 8/1997 | Moo-Young |
| 5,688,519 A | 11/1997 | Leonard |
| 5,888,533 A | 3/1999 | Dunn |
| 5,945,115 A | 8/1999 | Dunn et al. |
| 6,120,789 A | 9/2000 | Dunn |
| 8,173,148 B2 | 5/2012 | Dadey et al. |
| 8,357,388 B2 | 1/2013 | McKay |
| 8,722,037 B2 | 5/2014 | Veenstra et al. |
| 9,283,212 B2 | 3/2016 | O'Neil |
| 9,399,018 B2 | 7/2016 | Hudson et al. |
| 9,980,850 B2 * | 5/2018 | Baillie ............ A61K 47/24 |
| 2006/0003008 A1 | 1/2006 | Gibson et al. |
| 2008/0096910 A1 | 4/2008 | Guarnieri |
| 2008/0112892 A1 | 5/2008 | Veenstra et al. |
| 2011/0086083 A1 | 4/2011 | Biggs et al. |
| 2014/0342985 A1 | 11/2014 | Gibson et al. |
| 2014/0343080 A1 | 11/2014 | Steven et al. |
| 2016/0220498 A1 * | 8/2016 | Soni ............ A61K 9/5031 |

OTHER PUBLICATIONS

Maddox et al. (Etonogestrel, Another treatment option for contraception, Drug Forecast, vol. 33, No. 6, Jun. 2008. (Year: 2008).*

"PCT Search Report and Written Opinion, PCT/US2017/054436", dated Dec. 26, 2017.

PCT Search Report and Written Opinion, PCT/US2017/054466, dated Feb. 22, 2018.

"Sterile Single-Use plastic Syringes", European Pharmacopoeia 5.0. Section 3.2.8, Jan. 2005, 314-315.

Darney, et al., "Clinical Evaluation of the Capronor Contraceptive Implant: preliminary report.", Am J Obstet Gynecol. 160(5 Pt 2), May 1989, 1292-5.

Darney, et al., "Subdermal Progestin Implant Contraception", Curr Opin Obstet Gynecol 3(4), Aug. 1991, 470-6.

Guarnieri, "Subcutaneous implants for long-acting drug therapy in laboratory animals may generate unintended drug reservoirs", J. Pharm. Bioallied Sci. 6(1), 2014, 38-42.

Gupta, et al., "Multicenter Clinical Trial of Implanted Norethindrone Pellets for Long-Acting Contraception in Women", Contraception 30(3), 1984, 239-252.

Joshi, et al., "Phase I Comparative Clinical Trial with Subdermal Implants—Bioadsorbable Levonorgestrel or Norethisterone Pellet Fused with Cholesterol", Contraception 31(1), 1985, 71-82.

Singh, et al., "Biodegradable norethindrone (NET:cholesterol) contraceptive implants: phase II-A: a clinical study in women.", Contraception. 55(1), Jan. 1997, 23-33.

* cited by examiner

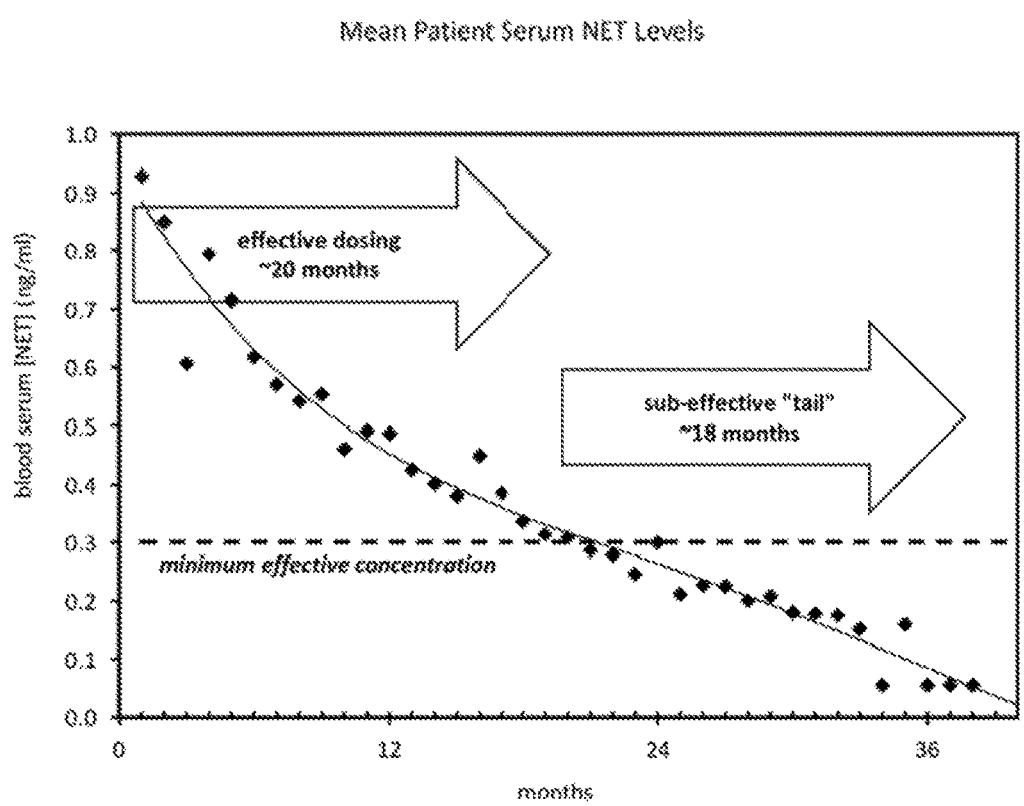

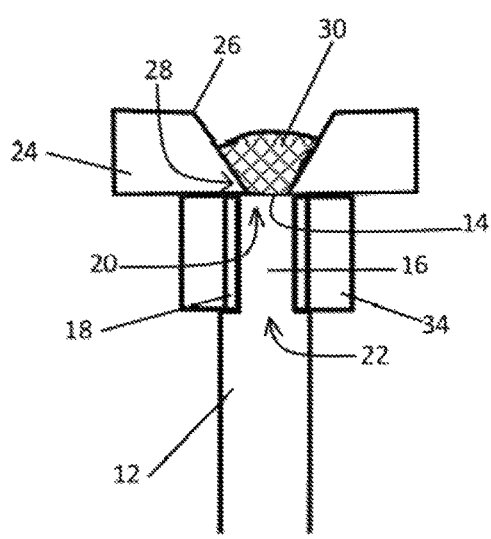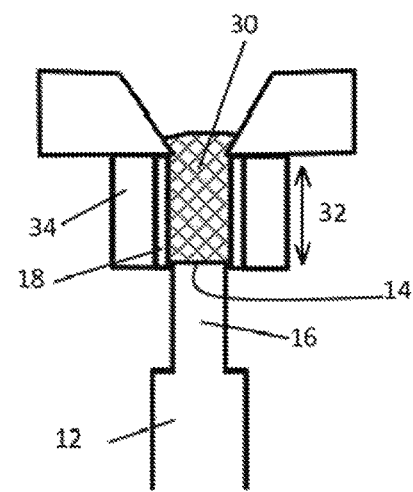

Effect of Pellet Length
Core Type Pellets

Effect of Pellet Length
Shell Type Pellets

BIOERODIBLE CONTRACEPTIVE IMPLANT AND METHODS OF USE THEREOF

CROSS-REFERENCE TO RELATED APPLICATIONS

This application is a continuation of U.S. patent application Ser. No. 15/720,845, filed Sep. 29, 2017, which issued on May 29, 2018 as U.S. Pat. No. 9,980,850 and claims priority under 35 U.S.C. § 119(e)(1) to provisional U.S. Patent Application Ser. No. 62/401,167, filed Sep. 29, 2016, the disclosure of which is incorporated by reference herein.

BACKGROUND OF THE INVENTION

(1) Technical Field

The invention relates generally to controlled release drug delivery systems, and more particularly relates to controlled release contraceptives. The invention finds utility in the fields of drug delivery, pharmaceuticals, medicine, and public health.

(2) Description of Related Art

Many types of contraceptive formulations and drug delivery systems have been developed and commercialized over the years. The oral formulation Enovid 10, colloquially referred to as "the pill," was approved for use in the United States in 1960, and was the first combined oral contraceptive (COC). Enovid 10 contained a combination of an estrogenic steroid, mestranol, at 9.85 mg, and a progestogen, norethynodrel, at 150 µg. At the time, it was known that birth control could be achieved with progestogen monotherapy, but the estrogenic component was added to enhance contraceptive efficacy and regulate vaginal bleeding. Enovid 10 was administered on a daily basis, 21 days out from a woman's menstrual cycle.

The original oral contraceptive formulation was later modified to reduce serious side effects, particularly an increased incidence of venous thromboembolism (VTE), which has been attributed for the most part to the estrogenic agent (the thrombotic risk was found to increase with increasing doses of the estrogen). Accordingly, later oral contraceptives contained a significantly lower dose of the estrogenic component, generally ethinyl estradiol (EE), on the order of 20 µg to 50 µg or even lower. In some subsequent contraceptive formulations, the more potent estrogenic agent 17β-estradiol ($E_2$) was substituted for EE, with chemical modifications of the compound, including micronization and esterification, made to improve its oral bioavailability. See Fruzzetti et al. (2012) *Gynecol. Endocrinol.* 28(5): 400-408 and Kuhnz et al., "Pharmacokinetics of Exogenous Natural and Synthetic Estrogens and Antiestrogens" in Oettel et al., Eds., *Handbook of Experimental Pharmacology, Estrogens and Antioestrogens II* (Berlin: Springer-Verlag, 1999).

In addition to oral contraceptives, a host of alternative contraceptive formulations and devices have been developed, including injectable contraceptives and intrauterine devices (IUDs). While there are many effective methods of contraception available today, there is an ongoing need for a method and/or formulation that fills a distinct gap in the current contraceptive mix, i.e., a contraceptive that is intermediate in duration of efficacy between existing injectable contraceptives and longer-acting methods, such as implants and IUDs, providing reliable contraceptive protection for on the order of one to two years. An ideal formulation would also be: "forgettable" insofar as its effectiveness would not depend on user compliance each day or at each coital act; removable before complete absorption, for women who decide to terminate use of birth control; and biodegradable, so that removal is not required.

Contraceptive implants were first studied in efforts to develop such a formulation. One of the first studies of biodegradable implants for the delivery of contraceptive drugs began in the 1970s with experiments using a biodegradable polyorthoester drug delivery matrix developed by the ALZA Corporation and marketed under the trade name Alzamer™ (initially Chronomer™). The polyorthoester matrix was advantageous insofar as it was possible to control degradation via both hydrolysis and surface erosion, but preclinical testing studies with norethindrone and levonorgestrel were discontinued due to local irritation experienced by study participants. See Heller et al. (1990) *Biomaterials* 11:659-665; and Pharriss et al. (1976) *J. Reprod. Med.* 17:91-97.

Early work using cholesterol as an excipient in contraceptive implants began with initial trials in non-human primates in the late 1970s. Norethindrone was fused with cholesterol in a flash melting process. Several human clinical trials were conducted with fused cholesterol-hormone pellets in the 70s, 80s and 90s; see, e.g., Beck et al. (1978) *Contraception* 18:497-505; Gupta et al. (1984) *Contraception* 30:239-252; Joshi et al. (1985) *Contraception* 31:71-82; and Odlind et al. (1979) *Contraception* 19:639-648. A cholesterol-based norethindrone implant (Annuelle™) developed by Endocon, Inc. underwent a Phase II pharmacokinetics/pharmacodynamics and safety trial, but the release profile was longer than the planned 12-month duration, and there were additional complications as well; see Raymond et al. (1996) *Fertility and Sterility* 66:954-961.

Most of the work on contraceptive implants to date has involved the use of aliphatic polyesters, including polylactic acid (PLA), polyglycolic acid (PGA), polycaprolactone (PCL) and the copolymer of PLA and PGA, poly (lactic-co-glycolic acid) (PLGA); see Pitt et al. (1981) *NIDA Res. Monogr.* 28:232-53. Such materials have been viewed as attractive candidates because their degradation products are naturally occurring metabolites, i.e., lactic and glycolic acid. Additionally, these polymers have been used in products with prior regulatory approval, including sutures, meshes, screws, pins and plates for various surgical applications and for drug delivery. This precedent would likely shorten the regulatory pathway for the approval of future products containing these polymers. Another benefit of these materials is that copolymers such as PLGA can be engineered to have different monomer ratios allowing control of degradation rates. A polycaprolactone-based contraceptive implant, Capronor™, was developed in the 1980s, designed to release levonorgestrel for a period in the range of 12 to 18 months and then degrade. While not evidencing any problems with structural integrity, the product was abandoned because of skin irritation experienced by study participants, stability problems during storage, and a long release tail, explained infra.

More recently, contraceptive implants have been developed for the sustained release of etonogestrel (Implanon®), as well as the newer radio-opaque version, Nexplanon®, from Merck & Co.), which are intended to provide contraceptive protection for up to three years. See Maddox et al. (2008) P&T 33(6):337-347, the prescribing information for Implanon and Nexplanon, and U.S. Pat. Nos. 4,957,119, 8,722,037 and 8,888,745. Like many other implants, however, Implanon and Nexplanon must be surgically removed as they are composed of non-bioerodible materials.

Accordingly, while these contraceptive dosage forms were found to provide reasonably effective contraceptive protection, there were numerous problems. Aside from the other issues noted in the above discussion, the need for removal of the implant represents more than just an inconvenience. In many areas of the world, women do not have ready access to reliable, quality surgical removal services, or to facilities that could treat ensuing medical complication. Issues can arise with the formation of fibrous tissue around the implant, the failure to locate implants that may have been inserted too deeply, pain, tissue damage, local infection, and nerve damage. Rumor or knowledge of difficulties associated with implant removal can deter women from choosing implants as a contraceptive method despite other inherent advantages.

In addition, some implants have given rise to a long interval of time subsequent to the last measured pharmacologically effective serum level of the active agent (i.e., a serum level effective to provide reliable contraceptive protection), during which time interval the active agent was still detectable—and thus continuing to be released by the dosage form—but not present at a serum level sufficient to provide for reliable contraception. See Raymond et al. (1996), supra, at 960. In the aforementioned study, involving a biodegradable implant, the dosage of the contraceptive agent fell below the minimum effective level for some time, in some cases for as long as 18 months. This is an unacceptably long time period during which contraceptive agent is still being delivered but at a dosage that is too low to provide a contraceptive effect. Other contraceptive implants that are bioerodible have also resulted in a "tail" or "tail period" as well, meaning that there is a significant interval of time prior to complete bioerosion of the implant in which the contraceptive agent is being released, but at a dose below that needed to provide effective contraceptive protection. Aside from the failure of the implant to provide contraceptive efficacy during this time, there is a concern that pregnancies conceived during the tail period (i.e., in the presence of low, sub-effective active agent levels) may have a danger of being ectopic. See Callahan (et al. (2015) *Contraception* 92:514-522.

There is, accordingly, an ongoing need in the art for a contraceptive product that addresses the above drawbacks. An ideal extended release contraceptive implant would be (1) bioerodible, thereby obviating the need for surgical removal, (2) composed of non-toxic, naturally occurring materials, (3) simple, inexpensive, and straightforward to manufacture, without need for many steps, complicated equipment, toxic reagents, or a great deal of time, and (4) physically and chemically stable during storage, handling, sterilization, handling, and a possible early removal procedure. An ideal contraceptive implant product would also provide contraceptive protection over an extended time period, e.g., over a year or more, and also have a reduced tail period relative to those observed with earlier contraceptive implants.

BRIEF SUMMARY OF THE INVENTION

Accordingly, the invention is directed to the aforementioned need in the art and, in one embodiment, provides a contraceptive drug delivery system in the form of a subdermally implantable pellet that provides for controlled, sustained release of a contraceptive agent throughout an extended drug delivery time period. The pellet comprises an amount of a contraceptive agent which, following subdermal implantation of at least one of the pellets into a female individual, results in a serum level of the contraceptive agent sufficient to provide contraceptive efficacy during the extended drug delivery time period. The contraceptive agent may be a progestogen, or it may be a combination of active agents such as a combination of a progestogen and an estrogen. The pellet is bioerodible in situ, so that there is no need for surgical removal of the pellet at the end of the drug delivery period. That is, any bioerosion products are water soluble, bioresorbable, or both, so as to dissolve in or be absorbed by the body.

In one aspect of this embodiment, the contraceptive drug delivery system is comprised of more than one pellet.

In another aspect of this embodiment, the contraceptive drug delivery system comprises two to six pellets, e.g., four or five pellets.

In another aspect of this embodiment, the pellet as a whole is lipophilic, meaning that the total of any hydrophilic components represents less than 50 wt. % of the pellet.

In a related aspect, the total of any hydrophilic components represents less than 45 wt %, less than 40 wt. %, less than 35 wt. %, less than 30 wt. %, less than 25 wt. %, less than 20 wt. %, less than 15 wt. %, less than 10 wt. %, or less than 5 wt. % of the pellet. It will thus be appreciated that the pellet may be substantially free of hydrophilic components.

In another aspect of this embodiment, the pellet comprises a solid at the temperature in the range of about about 35° C. to about 40° C. This ensures that the pellet will be in substantially solid form in the body and under storage conditions. In a preferred embodiment, a hot melt pellet manufacturing method is employed, as described infra, in which case the pellet composition should be flowable at a selected temperature in the range of about 50° C. to about 250° C.

In an additional aspect of this embodiment, the pellet contains an excipient composition that includes at least one excipient. Each pellet excipient should be (a) a water-soluble and/or bioresorbable compound, or (b) transformed in situ to water-soluble and/or bioresorbable species, i.e., during pellet bioerosion, or both (a) and (b). In a related aspect of this embodiment, pellet excipients are selected from naturally occurring materials, where the naturally occurring materials may be obtained from a biological source or chemically synthesized in whole or in part.

In another aspect of this embodiment, the pellet has an elongated form. For example, the pellet may comprise a rod-shape dosage form that may be substantially cylindrical.

In another aspect of this embodiment, the pellet is monolithic, comprising a substantially homogeneous matrix with the contraceptive agent dispersed therein.

In another aspect of this embodiment, the pellet is composed of two or more discrete regions each having a different composition, e.g., compositions that differ with respect to components, component amount, component concentration, or the like. For example, the pellet may be composed of two regions, with a first region containing the contraceptive agent and the second region containing only inactive ingredients. As another example, the first region and the second region may both contain the same contraceptive agent but with the agent present in different amounts and/or at different concentrations. As a further example, the first and second regions may contain two different contraceptive agents.

In a related aspect, the pellet is composed of a core-and-shell type of dosage form, where the first discrete region is the core and the second discrete region is the shell. With an elongated dosage form, the first region may be an inner core having a length, a surface along the length, a first end, and a second end, and the second region may be an outer shell enclosing the surface of the inner core along its length but not the first end or the second end, such that the core has exposed surface area at the first and second ends. This type of structure may be one wherein: at least about 80 wt. % (e.g., at least about 90 wt. %, including 100%) of the contraceptive agent in the pellet is in the core (referred to herein as a "core-type" pellet); at least about 80 wt. % (e.g., at least about 90 wt. %, including 100%) of the contraceptive agent in the pellet is in the shell (referred to herein as a "shell-type" pellet); or contraceptive agent is present in both the core and the shell with greater than about 20 wt. % of the contraceptive agent present in each region.

In another aspect of this embodiment, the extended drug delivery time period includes an effective drug delivery time period, during which the contraceptive agent is released at a dosage sufficient to provide contraceptive efficacy, where the effective drug delivery time period is in the range of about three months to about four years, e.g., about six months to about four years; about six months to about three years; or about one year to about three years, such as about 18 months.

In another aspect of this embodiment, the extended drug delivery time period includes two time periods, a first time period that is an effective drug delivery period as defined in the preceding paragraph, and a subsequent, second time period that is a sub-effective drug delivery period during. That is, the pellet releases the contraceptive agent during the first, "effective drug delivery period" at a dosage sufficient to provide contraceptive efficacy, but thereafter, during the "sub-effective drug delivery period," the pellet continues to release the contraceptive agent but at a dosage that is less than sufficient to provide contraceptive efficacy (where effective and sub-effective dosages correlate with effective and sub-effect serum levels, respectively). The sub-effective drug delivery period, during which the pellet continues to release the active agent but at a dosage below an effective contraceptive dosage, is sometimes referred to as a "tail period" and, in a preferred embodiment, is at most about 12 months. In a related aspect of this embodiment, the tail period is at most about 9 months.

In another embodiment, one or more aspects of the pharmacokinetic profile of the subdermally implantable pellet are selected and "tuned" during manufacture, using at least one pellet property selected from width, length, diameter, surface area, size, composition, hardness, and degree of crystallinity.

In a related aspect of this embodiment, the pellet includes a release rate controlling agent as an excipient, wherein the release rate controlling agent has a water solubility effective to increase the release rate of the active agent from the pellet or to decrease the release rate of the active agent from the pellet, relative to the release rate of the active agent from the pellet in the absence of the release rate controlling agent.

In another related aspect of this embodiment, the pellet includes a softening agent as an excipient. The selection of softening agent, the amount of the softening agent, or both, are selected so that the overall hardness of the pellet is as desired, e.g., for purposes of implantation, palpation, or the like. In a further related aspect of this embodiment, the softening agent is a crystallinity modulator.

In another embodiment of the invention, a method is provided for administering a contraceptive agent to a female individual in a sustained release manner over an extended drug delivery time period, where the method involves: providing a drug delivery system comprising a subdermally implantable, bioerodible pellet that continuously releases a contraceptive agent throughout an extended drug delivery time period; and subdermally implanting the drug delivery system into a female individual. Products and by-products of pellet bioerosion dissolve or are resorbed, obviating the need for surgical removal.

In a related aspect of this embodiment, the method involves treatment of a female individual having a condition, disease or disorder that is responsive to the sustained release administration of the contraceptive agent. In a further related aspect, the method comprises female hormone replacement therapy.

BRIEF DESCRIPTION OF THE DRAWINGS

FIG. 1 (PRIOR ART) is a graph showing the extended time period during which an implanted norethindrone pellet was found to release sub-effective but detectable concentrations of the active agent (adapted from Raymond et al. (1996) *Fertil. Steril.* 66(6):954-61).

FIG. 2A schematically illustrates a pellet manufacturing assembly used to make a monolithic pellet of the invention, prior to drawing the pellet composition into the pelleting tube; FIG. 2B schematically illustrates the pellet manufacturing assembly subsequent to drawing the pellet composition into the pelleting tube.

DETAILED DESCRIPTION OF THE INVENTION

Figure 3A:
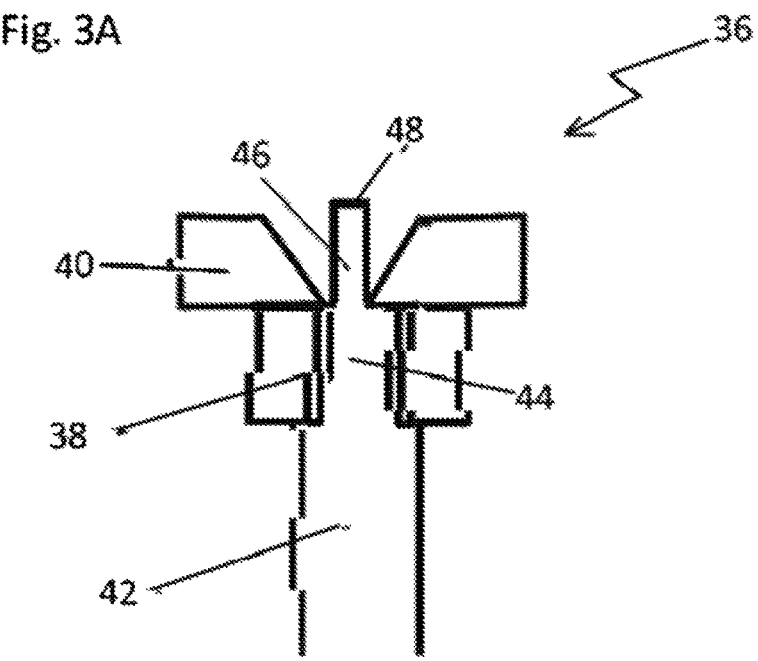
FIG. 3A schematically illustrates a pellet manufacturing assembly used to make a core-and-shell type pellet of the invention.
Figure 3B:
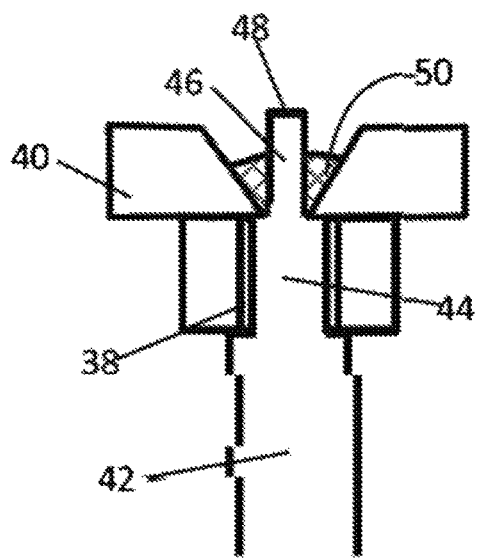
FIG. 3B illustrates the core-and-shell type pellet manufacturing assembly of FIG. 3A with the shell composition having been introduced into the funnel above the pelleting tube.

I. Definitions and Terminology:

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "a contraceptive agent" refers not only to a single contraceptive agent but also to two or more contraceptive agents that may or may not be combined in a mixture; "an excipient" refers to a single excipient or two or more excipients, which, again, may or may not be combined in a mixture; and the like.

The term "bioerodible" is used herein in a manner synonymous with "biodegradable," and includes any mechanism that may contribute to the gradual reduction in mass of an implanted pellet throughout an extended drug delivery period. Thus, a bioerodible pellet may degrade as a result of in vivo forces interacting with the pellet surface such as shear forces; cellular action, e.g., endocytosis and cell-mediated dispersion of microscopic particles released from the pellet during cell migration; and gradual dissolution of one or more pellet components. Throughout this disclosure and claims, the use of the term "bioerodible" to characterize a subdermally implantable pellet of the invention also indicates that the pellet bioerodes in situ in a manner that obviates the need for surgical removal after completion of drug release (although earlier removal may sometimes be desirable for one reason or another), insofar as all pellet bioerosion products are either water soluble, bioresorbable, or both. Accordingly, the term "bioerodible," in a first instance, refers to a completely bioerodible pellet, which may be, for example, a pellet entirely composed of an active agent that is gradually released in situ. In a second instance, and more typically, the term "bioerodible" refers to a pellet composed of a contraceptive agent and an excipient composition containing one or more excipients wherein each excipient is (a) a water-soluble and/or bioresorbable compound, or (b) transformed in situ to water-soluble or bioresorbable species, or (c) both (a) and (b), so that all products of pellet bioerosion are dissolved or absorbed within the body, and thus naturally and benignly cleared by the body.

The term "controlled release" refers to a drug-containing formulation or dosage form, e.g., subdermal implant, which does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). "Controlled release" for the present purpose includes "sustained release" (synonymous with "extended release"), referring to a formulation that provides for gradual release of an active agent over an extended period of time.

The term "subdermal" to refer to the intended in situ location of the implanted pellet means that the pellet is introduced at an interior body location beneath the skin, where release of the active agent occurs beneath the skin and enters the systemic circulation, i.e., the implantable pellets of the invention provide for "systemic" drug delivery. Subdermal implantation includes subcutaneous implantation as well as deeper implantation (the latter generally being the case with hormone replacement therapy, for example, wherein the implant is typically injected into the deeper fatty layers of the stomach or buttocks rather than subcutaneously).

The term "lipophilic" as used herein refers to a pellet or to a pellet segment (e.g., shell or core) containing less than 50 wt. % hydrophilic materials, where "hydrophilic" materials in this context are materials having an aqueous solubility greater than about 50 mg/mL (5 wt. %). It will be appreciated that a pellet, core, or shell that contains 50 wt. % or more of a lipophilic active agent is lipophilic as a result, even if the pellet, core, or shell contains one or more hydrophilic excipients, because the hydrophilic excipients necessarily represent less than 50 wt. % of the pellet.

The term "water soluble" refers to a compound having an aqueous solubility greater than about 30 mg/mL (i.e., 3 wt. %), typically greater than about 50 mg/mL (i.e. 5 wt. %).

A "lipidic material" refers to a composition comprising one or more lipidic compounds that in combination represent greater than 50 wt. % of the lipidic material, wherein "lipidic compounds" include lipids per se, i.e., naturally occurring lipids, whether obtained from a biological source or chemically synthesized in whole or in part; lipid analogs; lipid derivatives; lipid conjugates; and the like.

The term "flowable" refers to a composition that has been transformed, by the application of heat and/or other means (e.g., formation of a suspension, slurry, or the like), from a solid or substantially solid form to a composition that flows. Normally, the transformation is effected thermally, within the context of a hot melt manufacturing process, in which case the flowable composition so provided is also referred to herein as "molten." The approximate temperature at which a pellet, shell, or core composition undergoes this transition is referred to herein as the "transition temperature." The transition temperature may be seen as a melting temperature, although since the compositions herein are usually mixtures, composed of two or more different compounds, there is no definite melting point (unless characterized using an empirical method such as the determination of dropping point or slip point).

The term "substantially homogeneous" indicates a material in the form of a mixture of two or more components in which the material is substantially uniform throughout, with any two discrete regions within the material differing by at most about 20%, preferably by at most about 10%, and most preferably by at most about 5%, with respect to a chemical or physical property of the material, such as the presence or absence of a component, the concentration of a component, the degree of hydrophilicity or lipophilicity, density, crystallinity, or the like.

"Pharmacologically active" (or simply "active"), as in a "pharmacologically active" analog, derivative or other version of an active agent, refers to a compound having the same type of pharmacological activity as the parent compound and approximately equivalent in degree. Therefore, when referring to a contraceptive agent, whether specified as a particular compound (e.g., etonogestrel or levonorgestrel) or a compound class (e.g., a progestogen or an estrogen), the term used is intended to encompass not only the specified molecular entity or entities but also pharmaceutically acceptable, pharmacologically active analogs and derivatives thereof, including, but not limited to, salts, esters, prodrugs, conjugates, active metabolites, crystalline forms, enantiomers, stereoisomers, and other such derivatives, analogs, and related compounds.

In particular, as an example, when referring to a specific female hormone, i.e., a progestogen or an estrogen, it is to be understood that the term not only refers to the agent per se in unmodified form, but also refers to pharmacologically active, pharmaceutically acceptable esters of the agent. For instance, a reference to "hydroxyprogesterone" (17α-hydroxyprogesterone) includes not only hydroxyprogesterone per se but also pharmacologically active, pharmaceutically acceptable hydroxyprogesterone esters such as hydroxyprogesterone caproate, hydroxyprogesterone acetate, and hydroxyprogesterone heptanoate.

It should also be noted, with regard to the contraceptive agent herein, that the "progestogen" can be progesterone, i.e., the naturally occurring progestogen, or it can be another naturally occurring progestogen or a synthetic or semi-synthetic progestogen. Synthetic and semi-synthetic progestogens are often referred to as "progestins." Similarly, the term "an estrogenic compound" or "an estrogen" is used herein to refer to naturally occurring estrogens as well as to synthetic and semi-synthetic estrogens.

The terms "effective amount" and "therapeutically effective amount" of an agent, compound, or composition refer to an amount that is nontoxic and effective for the intended purpose, e.g., contraception, hormone replacement therapy, or the like.

By "contraceptive efficacy" is meant contraceptive protection having less than a 2% failure rate, preferably less than a 1% failure rate, less than a 0.5% failure rate, and less than a 0.25% failure rate, such as a failure rate of 0.1% or lower.

The term "approximately" in any context is intended to connote a possible variation of at most about 20%. Generally, the term connotes a possible variation of at most about 10%, preferably at most about 5%. The term "substantially" is defined in an analogous manner.

An "excipient" herein refers to any component within the drug delivery system that is an inactive ingredient, such that all components other than the contraceptive agent are referred to herein as "excipients." Any excipient used should be "pharmaceutically acceptable," meaning not biologically or otherwise undesirable, so that that the excipient can be incorporated into a dosage form administered to a patient without causing any significant undesirable biological effects or interacting in a deleterious manner with any other components of the dosage form. "Pharmaceutically acceptable" excipients herein meet the criteria set out in the Inactive Ingredient prepared by the U.S. Food and Drug Administration, and, preferably, have also been designated "Generally Regarded as Safe" ("GRAS").

The terms "treating" and "treatment" as used herein refer to reduction in severity and/or frequency of symptoms, elimination of symptoms and/or underlying cause, and improvement or remediation of damage, e.g., reduction in the number and/or extent of menopausal symptoms with a patient being given hormone replacement therapy using the drug delivery system of the invention. Unless otherwise indicated, the terms "treating" and "treatment" as used herein encompass prevention of symptoms as well, for instance in the administration of hormone replacement therapy to a perimenopausal woman.

As used herein, the terms "subject," "individual," and "patient" refer to any female individual for whom the present contraceptive drug delivery system is intended and to whom a contraceptive agent is administered as described herein. The female individual may be human or a non-human animal, generally a mammal. Veterinary use of the present drug delivery system is thus envisioned.

II. Pellet Composition:

The contraceptive drug delivery system of the invention is composed of at least one subdermally implantable, bioerodible pellet that provides for controlled, sustained release of a contraceptive agent contained therein during an extended drug delivery time period. In one embodiment, each subdermally implantable pellet contains a single type of contraceptive agent, a progestogen; in a subset of this embodiment, the implantable pellet contains a single progestogen. Suitable progestogens that can be administered using the delivery system and method of the invention include progesterone per se, i.e., the active natural progestogen that is found in the corpus luteum, placenta, and adrenal cortex. Other progestogens that can be effectively administered as contraceptive agents using the presently disclosed system and method are other naturally occurring progestogens, synthetic progestogens, and semi-synthetic progestogens; synthetic progestogens and semi-synthetic progestogens are known in the art as "progestins." Specific examples of progestogens useful in conjunction with the invention include, without limitation, the following:

21-acetoxypregnenolone;
allylestrenol;
anagestone (17α-hydroxy-6α-methylpregn-4-en-20-one);
anagestone 17α-acetate;
chlormadinone;
chlormadinone 17α-acetate;
chloroethynyl norgestrel;
cyproterone;
cyproterone 17α-acetate;
desogestrel;
dienogest;
dimethisterone (6α,21-dimethylethisterone);
drospirenone (1,2-dihydrospirorenone);
ethisterone (17α-ethinyltestosterone or pregneninolone);
ethynerone;
etynodiol diacetate (norethindrol diacetate);
etonogestrel (11-methylene-levo-norgestrel; 3-keto-desogestrel);
gestodene;
hydroxyprogesterone (17α-hydroxyprogesterone);
hydroxyprogesterone caproate;
hydroxyprogesterone acetate;
hydroxyprogesterone heptanoate;
levonorgestrel;
lynestrenol;
medrogestone (6,17α-dimethyl-6-dehydroprogesterone);
medroxyprogesterone;
medroxyprogesterone acetate;
megestrol;
megestrol acetate;
segesterone acetate;
nomegestrol;
nomegestrol acetate;
norethindrone (norethisterone; 19-nor-17α-ethynyltestosterone);
norelgestromin (17-deacetylnorgestimate);
noretynodrel;

norgestrienone;
progesterone; and
retroprogesterone.

Progestogens within this group that are sometimes preferred include, by way of example only, desogestrel, dienogest, drospirenone, ethisterone, etonogestrel, gestodene, levonorgestrel, medroxyprogesterone, megestrol, norethindrone, norgestimate, and esters of any of the foregoing, when the compound allows for esterification (e.g., medroxyprogesterone acetate, megestrol acetate, norethindrone acetate, etc.). Within the aforementioned group, the progestogenic agents that are particularly preferred include etonogestrel and levonorgestrel.

In another embodiment, the contraceptive agent comprises a combination, e.g., a mixture, of a progestogen and an additional contraceptive agent. In this embodiment, the additional contraceptive agent is usually an estrogen, i.e., an estrogenic compound, with the ratio of the progestogen to the estrogen selected to correspond to the progestogen-to-estrogen ratios of commercially available dual hormone contraceptive products, regardless of the mode of administration. Suitable estrogenic compounds will be known to those skilled in the art and are described in the literature, and include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Generally preferred such compounds include 17β-estradiol, estetrol, estriol, estrone, ethinyl estradiol, mestranol, moxestrol, quinestrol, conjugated estrogens, and combinations thereof.

When any of the aforementioned progestogens are referred to without mention of a salt, ester, or other derivative or analog, it should again be emphasized that reference to the active agent per se includes such derivatives and analogs. Thus, when the term "cyproterone" is used herein, the agent referred to may be cyproterone per se or a cyproterone ester such as cyproterone 17α-acetate, when the term "medroxyprogesterone" is used, the agent referred to may be medroxyprogesterone per se or a medroxyprogesterone ester such as medroxyprogesterone acetate, and the like.

The amount of the contraceptive agent in a drug delivery system of the invention comprising a subdermally implantable pellet is selected to result in serum levels of the contraceptive agent sufficient to provide contraceptive efficacy during the effective drug delivery time period, taking the release rate, length of the intended drug delivery time period, and specific contraceptive agent into account. It should be noted that although the drug delivery system may be composed of only one subdermally implantable pellet, it may also be composed of two to six pellets, e.g., four or five pellets. When the drug delivery system is composed of more than one pellet, the number of pellets implanted is also taken into account in determining the amount of contraceptive agent to incorporate into a single pellet. The optimum amount is preferably calculated for a drug delivery time period in the range of about three months to about four years, e.g., in the range of about six months to about four years; in the range of about six months to about three years; and in the range of about one year to about three years, for instance about 18 months. The total quantity of contraceptive agent in the subdermally implanted drug delivery system for an approximately 18-month drug delivery time period, in the case of etonogestrel and levonorgestrel, for example, will generally be in the range of about 5.0 mg to about 200 mg, typically in the range of about 5.0 mg to about 50 mg.

Drug loading may be in the range of about 20 wt. % to about 100 wt. %., preferably in the range of about 50 wt. % to about 99 wt. %, more preferably in the range of about 75 wt. % to about 95 wt. %. The aforementioned ranges pertain to the percentage of contraceptive agent in a monolithic pellet, or, for a core-type pellet or a shell-type pellet, the percentage of the contraceptive agent in the shell or core, respectively. Optimal drug loading may approximate 85 wt. %. The degree of drug loading can be altered to vary drug release profile as desired. As shown in Example 7, increasing the fraction of contraceptive agent in the pellet generally results in an increase in drug release rate.

The pellets may be wholly composed of active agent, but generally, and preferably, contain an excipient composition as well, where the excipient composition may be a single excipient or it may include two or more excipients. Excipients for incorporation into the present pellets along with the active agent should be selected so as to avoid compromising the bioerodibility of the pellet as a whole. This means that any excipients should be bioresorbable, water soluble, or both, and/or degrade or otherwise transform in situ, during bioerosion of the pellet, to bioresorbable and/or water-soluble species. Preferred excipients are naturally occurring compounds, which may be obtained from a biological source or chemically synthesized in whole or in part. One or more excipients may be hydrophilic, providing that the pellet as a whole is still lipophilic. For core-type pellets and shell-type pellets, both the core and the shell should be lipophilic, meaning that the core and shell each contain less than 50 wt. % hydrophilic materials, preferably less than 45 wt %, less than 40 wt. %, less than 35 wt. %, less than 30 wt. %, less than 25 wt. %, less than 20 wt. %, less than 15 wt. %, less than 10 wt. %, or less than 5 wt. % of the pellet. "Hydrophilic" materials, as noted previously, are materials having an aqueous solubility of at least about 3 wt. %, e.g., at least about 5 wt. %, or the like. For example, a pellet, core, or shell that contains a lipophilic active agent, with the lipophilic active agent representing at least 50 wt. % of the pellet, core, or shell, respectively, is necessarily lipophilic, insofar as the total hydrophilic components represent less than 50 wt. % of the pellet, core, or shell composition.

Excipients may or may not be solid at body temperature and under storage conditions, so long as: (1) the pellet as a whole is substantially solid at body temperature and during storage, i.e., at temperatures in the range of about 35° C. to about 40° C.; and (2) the pellet composition is flowable at a selected temperature in the range of about 50° C. to about 250° C., particularly when a hot melt manufacturing technique—such as the manufacturing process described herein—is used. In addition, excipients should be selected so that the pellet does not fracture or break during or after implantation. This may require inclusion of a softening agent as an excipient, e.g., lecithin. However, the pellet should still be hard enough so that it can be palpated after implantation, to confirm or determine location.

Suitable excipients include, but are not limited to, lipidic compounds, e.g., lipids per se, including naturally occurring lipids and lipids that are chemically synthesized in whole or in part; lipid analogs; lipid derivatives; lipid conjugates; and the like. Naturally occurring lipids and readily hydrolyzable esters of naturally occurring lipids are generally preferred lipidic excipients, insofar as such compounds facilitate bioabsorption and bioerosion to nontoxic molecular components. For example, a lipidic excipient may be a sterol, a sterol ester, or a combination thereof, including, without limitation, cholesterol, 7-dehydrocholesterol, cholestatrienol, cholestanol, cholesteryl acetate, desmosterol, dehydroergosterol, thiocholesterol, 3-keto-delta-5-cholestene, 7-methylenecholesterol, epicholesterol, lathosterol, lanosterol, dihydrocholesterol, 25-hydroxycholesterol, cholestane, cholestane diol, cholest-4-en-3-one, and zymosterol. In some embodiments, cholesterol is a preferred lipidic excipient herein.

Other lipidic compounds that can serve as excipients herein include, but are not limited to, the following: phospholipids such as phosphorylated diacyl glycerides, particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof, wherein each acyl group contains about 10 to about 22 carbon atoms and is saturated or unsaturated; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group of the fatty acid is replaced with an ester moiety —(CO)—OR wherein R is a $C_1$-$C_3$ alkyl moiety optionally substituted with one or two hydroxyl groups; fatty alcohols corresponding to the aforementioned fatty acids, wherein the carboxylic acid group of the fatty acid is replaced by a —$CH_2OH$ group; glycolipids such as cerebroside and gangliosides; oils, including animal oils such as cod liver oil and menhaden oil, and vegetable oils such as babassu oil, castor oil, corn oil, cottonseed oil, linseed oil, mustard oil, olive oil, palm oil, palm kernel oil, peanut oil, poppyseed oil, rapeseed oil, safflower oil, sesame oil, soybean oil, sunflower seed oil, tung oil, or wheat germ oil; and waxes, i.e., higher fatty acid esters, including animal waxes such as beeswax and shellac, mineral waxes such as montan, petroleum waxes such as microcrystalline wax and paraffin, and vegetable waxes such as carnauba wax.

A lipidic excipient may also be incorporated into the pellets in a combination or mixture of two or more excipients (including mixtures of two or more lipidic excipients), for example having different aqueous solubilities and/or with one of the excipients selected to serve a particular purpose (e.g., functioning as a softening agent). For example, a pellet may contain a combination of a lipidic excipient having a first aqueous solubility and a second excipient, which may or may not be lipidic, having a second aqueous solubility, where the first aqueous solubility is lower than the second aqueous solubility by at least 5%, typically by at least 10%. The weight ratio of the less soluble excipient to the more soluble excipient may be in the range of about 2:1 to about 100:1, more typically in the range of about 3:1 to about 50:1, and optimally about 3.5:1 to about 25:1, e.g., 4:1. The examples herein describe such excipient compositions, wherein cholesterol serves as the lipidic excipient with a first aqueous solubility and lecithin or a component thereof (e.g., phosphatidylcholine) serves as the second excipient.

Additional excipients that can be incorporated into the pellets instead of, or in addition to, a lipidic excipient as described above, include, without limitation, phospholipids and phospholipid mixtures, e.g., lecithin (a phospholipid mixture) and glycerophospholipids such as phosphatidylcholine, phosphatidylethanolamine, phosphatidylinositol, and phosphatidylserine; polyethylene glycols (PEGs) of different molecular weights, e.g., PEG-300, PEG-1000, PEG-4000, PEG-6000, and PEG-8000; PEG fatty acid esters such as PEG laurates, oleates, stearates, and the like; other gradually erodible synthetic polymers such as polylactides, polyglycolides, polycaprolactones, polyanhydrides, polyurethanes, polyesteramides, polyorthoesters, polyvinylpyrrolidone, and polyhydroxycellulose; polymers typically used to prepare hydrogels, e.g., polyvinyl alcohol, poly (hydroxyethyl methacrylate), and polyacrylic acid; glycerine and glycerinated gelatin; chitin and chitosan; and lower molecular weight excipients such as propylene glycol.

If desired, a radio-opaque material can be incorporated into the present drug delivery systems in order to enable X-ray visualization of the implanted pellets. Suitable radio-opaque materials for this purpose are known in the art and include, for instance, barium sulfate, titanium oxide, bismuth oxide, tungsten, and iodinated contrast agents (i.e., contrast based on the 2,4,6-triiodobenzene structure), with barium sulfate more commonly used. Any such radio-opaque material will generally represent in the range of about 2.5 wt. % to about 30 wt. % of a pellet, more typically about 2.5 wt. % to about 15 wt. % of a pellet.

III. Physical and Pharmacokinetic Attributes of the Pellet:

The pellets herein can be of any size, shape or structure that allow for ease of manufacture and implantation, and that contribute to or at least do not detract from the desired pharmacokinetic properties. Generally, for ease of manufacture and implantation, the pellets are rod-shaped, i.e., approximately cylindrical, with length, width, surface area, etc., selected to provide specific pharmacokinetic or other properties, such as drug release rate, drug release profile (i.e., the change in release rate over time), length of the effective drug delivery period, length of any tail period, and the like.

An elongated pellet of the invention may be substantially cylindrical. Such pellets will generally have a length in the range of about 2.0 mm to about 12.0 mm, and a diameter in the range of about 1.0 mm to about 3.5 mm. Typically, pellet length is in the range of about 3.5 mm to about 7.0 mm, with pellet diameter in the range of about 1.0 to about 3.2. In a preferred embodiment, the pellet length is in the range of about 4.0 mm to about 6.5 mm and the pellet diameter is in the range of about 1.3 mm to about 3.0 mm. Exemplary pellet dimensions thus include: diameter 2.8 mm, length 6.0 mm; diameter 2.8 mm, length 4.5 mm; diameter 2.8 mm, length 4.0 mm; diameter 1.7 mm, length 4.0 mm. Additional examples are given below.

In one embodiment, the pellet is monolithic, such that the pellet is comprised of a substantially homogeneous matrix with the contraceptive agent is dispersed therein, where "substantially homogeneous" is defined in Part (I) of this section. In such a case, the pellet may be essentially amorphous, or it may be crystalline or partially crystalline, preferably without any interior voids. To check a monolithic pellet for substantial homogeneity, the pellet can be divided into several, e.g., three to six, subsections, and each subsection weighed and dissolved in a known amount of solvent. Each dissolved subsection can then be analyzed using a standard technique, e.g., HPLC, and the relative quantities of components determined and compared to the results in the other subsections.

A standard monolithic pellet will have dimensions as described above.

Monolithic pellets generally have a density in the range of about 0.75 g/cm$^3$ to about 1.25 g/cm$^3$, as do pellets composed of two or more discrete regions, e.g., cores and shells in core-type and shell-type pellets herein. More typically, monolithic pellets typically have a density in the range of about 0.90 g/cm$^3$ to about 1.10 g/cm$^3$, and most typically in the range of about 0.95 g/cm$^3$ to about 1.05 g/cm$^3$.

In another embodiment, the pellet is composed of two or more discrete regions each having a different composition. That is, compositions in different regions may differ with respect to components of the composition, component amount, component concentration, or the like. For example, the pellet may be composed of a first region containing the contraceptive agent and a second region containing only inactive ingredients, i.e., excipients. As another example, the first and second region may contain the same contraceptive agent, but in different amounts and/or present at different concentrations. Discrete regions may also contain different active agents, including different contraceptive agents.

A preferred pellet structure composed of two or more discrete regions is a core-and-shell type of dosage form, where the first region is an inner core and the second region is a shell that partially or entirely encloses the core. With an elongated dosage form such as a cylindrical pellet, the first region may be an inner core having a length, a surface along the length, a first end, and a second end, and the second region may be an outer shell enclosing the surface of the inner core along its length but not the first end or the second end, such that the core has exposed surface area at the first and second ends. This type of structure may be one wherein: at least about 80 wt. %, e.g., at least about 90 wt. %, of the contraceptive agent in the pellet is in the core (a "core-type" pellet); at least about 80 wt. %, e.g., at least about 90 wt. %, of the contraceptive agent in the pellet is in the shell (a "shell-type" pellet); or contraceptive agent is present in both the core and the shell with greater than about 20 wt. %, e.g., greater than about 10 wt. %, of the contraceptive agent present in each region. In one embodiment, a core-type pellet is composed of an inactive shell with 100% of the contraceptive agent in the core. In another embodiment, a shell-type pellet is composed of an inactive core with 100% of the contraceptive agent in the shell.

Typical dimensions for core-shell structures, including core diameter and shell thickness, are as follows: core diameter, about 1.0 mm to about 2.0 mm, shell thickness about 0.3 mm to about 1.0 mm, and length about 4 mm to about 6.5 mm. Specific examples of core/shell structure dimensions include, without limitation: core diameter 1.7 mm, shell thickness 0.6 mm, length 4.5 mm; core diameter 1.9 mm, shell thickness 0.9 mm, length 4.5 mm; core diameter 1.7 mm, shell thickness 0.6 mm, length 5.5 mm; and core diameter 1.9 mm, shell thickness 0.9 mm, length 5.5 mm.

The inactive region of a core-type pellet or a shell-type pellet, whether shell or core, is composed of a bioerodible excipient composition as described earlier herein, with the inactive region containing less than about 20 wt. %, e.g., less than about 10 wt. %, of the total amount of contraceptive agent in the pellet. The pharmacologically active region of a core-type pellet or a shell-type pellet, i.e., the region containing at least about 80 wt. %, e.g., at least about 90 wt. % of the total amount of contraceptive agent in the pellet, may be entirely composed of the contraceptive agent, but is usually a mixture of a bioerodible excipient composition, as defined previously, and the contraceptive agent, where the contraceptive agent is dispersed within a matrix defined by the bioerodible excipient composition. The excipient composition of the inactive region and the excipient composition of the pharmacologically active region may or may not be the same, with respect to the number, type, and/or concentration of individual excipients.

Representative examples of shell and core drug delivery systems of the invention include, without limitation, the following:

Monolithic pellets 1.7 mm in diameter and 4.0 mm in length, containing 85 wt. % etonogestrel;

Monolithic pellets 1.7 mm in diameter and 4.0 mm in length, containing 85 wt. % levonorgestrel;

Monolithic pellets 1.7 mm in diameter and 4.0 mm in length, containing 85 wt. % desogestrel;

Monolithic pellets 1.7 mm in diameter and 4.5 mm in length, containing 95 wt. % etonogestrel;

Monolithic pellets 1.7 mm in diameter and 4.5 mm in length, containing 95 wt. % levonorgestrel;

Monolithic pellets 1.7 mm in diameter and 4.5 mm in length, containing 95 wt. % desogestrel;

Monolithic pellets 1.7 mm in diameter and 3.5 mm in length, containing 75 wt. % etonogestrel;

Monolithic pellets 1.7 mm in diameter and 3.5 mm in length, containing 75 wt. % levonorgestrel;

Monolithic pellets 1.7 mm in diameter and 3.5 mm in length, containing 75 wt. % desogestrel;

Monolithic pellets 2.8 mm in diameter and 5.5 mm in length, containing 85 wt. % etonogestrel;

Monolithic pellets 2.8 mm in diameter and 5.5 mm in length, containing 85 wt. % levonorgestrel;

Monolithic pellets 2.8 mm in diameter and 5.5 mm in length, containing 85 wt. % desogestrel;

Monolithic pellets 2.8 mm in diameter and 6.0 mm in length, containing 95 wt. % etonogestrel;

Monolithic pellets 2.8 mm in diameter and 6.0 mm in length, containing 95 wt. % levonorgestrel;

Monolithic pellets 2.8 mm in diameter and 6.0 mm in length, containing 95 wt. % desogestrel;

Monolithic pellets 2.8 mm in diameter and 5.5 mm in length, containing 75 wt. % etonogestrel;

Monolithic pellets 2.8 mm in diameter and 5.5 mm in length, containing 75 wt. % levonorgestrel;

Monolithic pellets 2.8 mm in diameter and 5.5 mm in length, containing 75 wt. % desogestrel;

Monolithic pellets 2.8 mm in diameter and 4.5 mm in length, containing 85 wt. % etonogestrel;

Monolithic pellets 2.8 mm in diameter and 4.5 mm in length, containing 85 wt. % levonorgestrel;

Monolithic pellets 2.8 mm in diameter and 4.5 mm in length, containing 85 wt. % desogestrel;

Monolithic pellets 2.8 mm in diameter and 4.0 mm in length, containing 75 wt. % etonogestrel;

Monolithic pellets 2.8 mm in diameter and 4.0 mm in length, containing 75 wt. % levonorgestrel; and Monolithic pellets 2.8 mm in diameter and 4.0 mm in length, containing 75 wt. % desogestrel.

Shell/core pellets with a core 1.6 mm in diameter, a shell 0.6 mm in thickness, and the pellet 5.5 mm in length, with the shell composed of 85 wt. % etonogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.5 mm in length, with the shell composed of 85 wt. % levonorgestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.5 mm in length, with the shell composed of 85 wt. % desogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % etonogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % levonorgestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % desogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % etonogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % levonorgestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % desogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % etonogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % levonorgestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % desogestrel, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % etonogestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % levonorgestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % desogestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % etonogestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % levonorgestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % desogestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 5.0 mm in length, with the core composed of 85 wt. % etonogestrel, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 5.0 mm in length, with the core composed of 85 wt. % levonorgestrel, 12 wt. % cholesterol, and 3 wt. % phosphatidylcholine, and the shell composed of 97 wt. % cholesterol and 3 wt. % phosphatidylcholine; and Shell/core pellets with a core 1.6 mm in diameter, a shell 0.6 mm in thickness, and the pellet 5.0 mm in length, with the core composed of 85 wt. % desogestrel, 12 wt. % cholesterol, and 3 wt. % phosphatidylcholine, and the shell composed of 97 wt. % cholesterol and 3 wt. % phosphatidylcholine.

In one embodiment, the tail period is at most about 12 months, preferably at most about 9 months, more preferably at most about 6 months, and ideally at most about 3 months. This contrasts with tail periods observed with prior implants, such as those described by Raymond et al. (1996) *Fertil. Steril.* 66(6):954-61), illustrated in FIG. 1 (prior art).

Various parameters can be adjusted to alter one or more other aspects of a pellet's pharmacokinetic profile, such aspects including, by way of example, release rate, release profile, duration of the extended drug delivery time period, and duration of the tail period. For instance, the rate of drug release can be controlled both by modulating the aqueous solubility of the pellet composition and by controlling the surface area of the pellet, as it is the pellet surface that is exposed to in vivo erosive forces. With monolithic implants, narrower and longer pellets generally have a shorter tail period. Monolithic thin pellets with length-to-width ratios (i.e., length-to-radius ratios for substantially cylindrical pellets) greater than about 5:1 provide for a gradual, evenly decreasing release rate. The release rate of contraceptive agent from a monolithic pellet can be controlled by the bioerosion rate of the excipient composition, made tunable using excipients with different aqueous solubilities, as alluded to earlier herein. That is, an excipient composition composed entirely of a lipidic material such as cholesterol will tend to bioerode more slowly than an excipient composition composed of a mixture of cholesterol and a second excipient having higher aqueous solubility, e.g., a selected phospholipid. The rate of release can thus be controlled by varying the relative amounts of a more water-soluble excipient and a less water-soluble excipient in an excipient composition.

For substantially cylindrical core/shell pellets composed of a slowly dissolving core and a more quickly dissolving shell that contains most or all of the contraceptive agent, the drug release profile abruptly ends as erosion from the lateral face breaks through to the underlying core. Unlike monolithic pellets, the exposed surface area of the drug-containing shell approaches a non-zero value as it bioerodes, thus avoiding the release tail. In these drug-containing shell pellets, the rate of drug release is controlled by the rate of shell bioerosion and by the pellet length. The duration of drug release is controlled by the shell thickness.

Placing the contraceptive agent in the core instead of the shell can also eliminate the tail if the rate of core erosion is significantly faster than that of the shell. Here, the exposed drug-containing surface is only at the cylinder bases and drug release remains relatively constant until the core erodes out of the longer-lasting shell. The shell and core release rates are tuned with the proper addition of a lipid with higher aqueous solubility than cholesterol per se, so that erosion from the lateral face of the shell does not allow breakthrough before the pellet core is fully released. To achieve this result, the shell thickness divided by the shell erosion rate must be greater than or equal to the core length divided by the core erosion rate. In these drug-containing core systems, the rate of drug release is dependent upon the rate of core dissolution and the surface area of the core bases, and the duration of release is controlled by the pellet length. An additional benefit of a drug-containing core can be approximately zero-order drug release.

IV. Contraceptive Method:

At the outset, the number of pellets to be implanted is determined, taking into account the particular contraceptive agent, the predetermined release rate, the intended drug delivery time period, and other factors within the knowledge of the medical practitioner prescribing or administering the contraceptive system.

The pellet or pellets are then subdermally implanted, usually in the upper arm, forearm, or thigh, and allowed to remain in place. Since the pellets are bioerodible, there is no need for surgical removal, although the pellets can be surgically removed, if desired, at some point prior to complete bioerosion.

V. Other Methods of Use:

The bioerodible, implantable pellets of the invention are also useful in providing controlled release delivery of a contraceptive agent to female individuals for purposes unrelated to contraception. For instance, the present drug delivery systems are useful in providing female hormone replacement therapy ("HRT"), in that the occurrence of symptoms or conditions resulting from a woman's altered hormone levels is mitigated or substantially prevented. HRT is useful to treat women for whom ovarian steroid production has been altered, either because of menopause, surgery, radiation treatment, or premature ovarian failure. The subdermally implantable pellets of the invention are also useful in providing for the ongoing, controlled release of a contraceptive agent to a female individual in need of such treatment for other reasons, e.g., treatment or prevention of osteoporosis, treatment of certain neurodegenerative diseases, treatment of mood disorders, and the like. Other conditions, disorders, and diseases that may be treatable using the drug delivery systems of the invention will be known to those of ordinary skill in the art and/or are described in the relevant texts and literature.

VI. Pellet Implantation:

One or more controlled release contraceptive pellets of the invention are subdermally implanted into a patient for long-term, sustained release administration of the contraceptive agent therein, as described throughout this specification. Generally, although not necessarily, the drug-containing pellets are positioned just under the skin. Methods and devices for insertion and positioning of subdermal implants are known in the art, and any suitable method or device can be used in conjunction with the invention. Examples of suitable implantation devices include trocar-like inserters, other commercially available implantation devices, and devices described in the patent literature such as in U.S. Pat. Nos. 4,223,674; 6,964,648; 7,214,206; 7,510,549; 7,850,639; and International Patent Publication No. WO 98/13092 A1. Other suitable implantation devices will be apparent to those skilled in the art and/or are described in pertinent texts and literature. Subdermal implantation methods and devices should be non-irritating and non-sensitizing, and should work relatively quickly.

VII. Pellet Manufacture:

Any method to manufacture the present pellets can be used so long as the compositional and physical requirements of the pellets so made are met. Manufacturing methods include, for example, compression molding, molding, hot melt extrusion, injection molding, and hot melt molding.

One example of a preferred method to manufacture the present pellets is a variation of the hot melt molding process, a hot melt "drawing" process that uses a pin to pull a substantially homogenous mixture of pellet substrate material out of a heated reservoir and into a heated channel, or tube, composed of an inert, heat-resistant material such as polytetrafluoroethylene ("PTFE"). The pellet material can then be cooled under "channel capping" conditions, i.e., conditions that allow the pellet to fully form without internal cavities or sinks. Channel capping involves withdrawal of the elongated pin from the interior of the formed pellet, when still warm, in a gradual manner that allows the interior of the pellet to fuse and contract.

The method can be modified to make core-type and shell-type pellets, by first drawing molten shell material from the reservoir into the channel and allowing it to harden somewhat, forming a shell between a narrow pin extension and the interior of the channel. After allowing some cooling, and wiping the reservoir clean before continuing, molten core material from the reservoir is then drawn into the solidified shell. After a brief cooling period, the solid core-and-shell pellet can be pushed out of the channel/tube.

FIGS. 2A and 2B illustrate a pellet manufacturing assembly that can be used to make monolithic pellets of the invention. As shown in FIG. 2A, the assembly 10 includes an elongated pin having a body 12, a tip 14, and a substantially cylindrical upper segment 16. The pin is used in conjunction with pelleting tube 18, which has an upper tube opening 20, an opposing lower tube opening 22, and an inner surface. Tube 18 has an inner diameter sized to provide a sealing fit between the inner surface and the upper segment of the pin. The assembly further includes a funnel 24 in the form of an inverted cone structure concentrically tapering from an upper rim 26 down to a narrow outlet 28 aligned with the upper tube opening 20. It will be appreciated that the a functionally equivalent reservoir can be substituted for the funnel, providing that the reservoir is large enough to contain the intended volume of the selected pellet composition and has an outlet that enables downward flow of the pellet composition in a molten state. The funnel and tube are therefore in fluid communication so that the flowable pelleting material can enter the tube from the funnel.

To manufacture a pellet, the pin tip 14 is inserted into tube 18 through lower tube opening 22, and the pin is then moved upward through the tube toward the funnel until the pin tip reaches the upper tube opening; the pin is shown positioned in this manner in FIG. 2A. At that point, the upper tube opening having been sealed with the upper segment of the pin, the pellet composition 30, containing a pharmacologically active agent, is placed into the funnel. The pellet composition may be placed into the funnel in molten, i.e., flowable, form, or it can be heated within the funnel until rendered flowable if a temperature control mechanism is operably connected to the funnel body. The pin is then partially withdrawn from the tube through the lower tube opening, such that the pin tip is lowered a selected distance 32 from the upper tube opening, as illustrated in FIG. 2B. This draws the molten pellet composition 30 down into the tube via a siphoning effect. After the pin tip has been lowered, the pellet composition is allowed to cool so as to form the hardened pellet within the tube. The pin is then completely removed from the tube, and the pellet removed using any suitable means. The pellet so formed has a pellet length corresponding to the distance that the pin tip is lowered, i.e., the "selected distance," and a pellet diameter defined by the inner diameter of the pelleting tube. In a preferred embodiment, the assembly includes a means for maintaining the pelleting tube in place, such as the collar 34 shown in FIGS. 2A and 2B.

To form a core-and-shell type of pellet, illustrated in FIGS. 3A through 3E, a pellet manufacturing assembly 36 includes a pelleting tube 38 and a funnel 40 as described above for monolith manufacture. In this case, however, an elongated pin 42 is used that is composed of two axially aligned, substantially cylindrical segments of different diameters that are longitudinally adjacent, with a wider lower segment 44 and a narrower upper segment 46 that terminates in the pin tip 48. In addition, the relative dimensions in this context are such that a sealing fit is provided between the inner surface of the tube and the wider, lower segment of the elongated pin, while, as indicated in FIG. 3A, the upper, narrower segment of the pin is significantly narrower than the inner diameter of the tube.

Figure 3C:
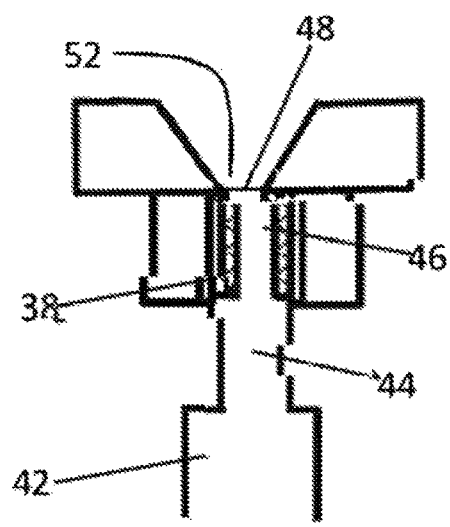
FIG. 3C illustrates the core-and-shell type pellet manufacturing assembly of FIG. 3B with the shell material has been drawn down into a concentric space within the pelleting tube.
Figure 3D:
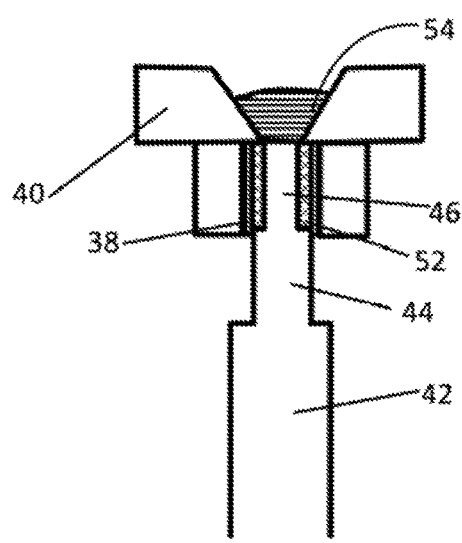
FIG. 3D illustrates the core-and-shell type pellet manufacturing assembly of FIG. 3C with the core composition having been introduced into the funnel above the pelleting tube.
Figure 3E:
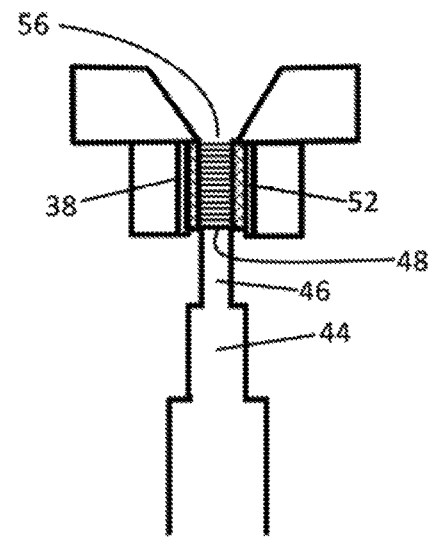
FIG. 3E illustrates the core-and-shell type pellet manufacturing assembly of FIG. 3D with the core composition having been drawn down into the cooled shell material within the pelleting tube.

Formation of a core-and-shell pellet begins by inserting the pin tip into the lower tube opening and moving the pin upward through the tube, toward the funnel, until the pin tip and then the upper pin segment protrude from the upper tube opening into the funnel; this configuration is shown in FIG. 3A. Upward, vertical movement of the pin through the tube in this way brings the lower pin segment into the tube, with the upper tube opening sealed as a result. As the shell is made first, the shell composition 50 is then placed into the funnel; see FIG. 3B. As with monolith manufacture, the shell composition may be heated until rendered flowable prior to placement in the funnel, or it can be heated within the funnel if a suitable heating apparatus is operably connected. To make the shell, the lower pin segment is gradually withdrawn from the tube through the lower tube opening, thus lowering the upper pin segment into the tube and simultaneously drawing the flowable shell composition into the concentric space forming between the upper, narrow segment of the pin and the inner surface of the tube as the pin is lowered; see FIG. 3C. The hot shell composition is allowed to cool, thereby hardening into a shell 52 formed around the upper segment of the pin, within the tube, as shown in FIG. 3C.

The core composition 54 (see FIG. 3D) is added into to the funnel 40 after cleaning, and is either in molten, flowable form prior to placement in the funnel or heated therein, as described above. The narrower, upper pin segment 46 is then gradually lowered within the tube, drawing the core composition down into the shell; see FIG. 3E. The core-and-shell pellet so formed is allowed to cool, with the molten core 56 fusing within the shell 52 during the cooling process, and harden to a degree sufficient to allow complete removal of the pin without any flow of pelleting material. The finished pellet can then be removed from the tube using any suitable means.

The methodology allows facile control over pellet dimensions, insofar as the diameter of the pellet formed is determined by the inner diameter of the tube, and the length of the pellet is determined by the extent to which the pin or individual segments thereof are lowered within the tube, before the pellet, core, or shell is allowed to cool and harden. It will therefore be appreciated that the method can be readily adapted to make pellets of different dimensions. That is, pellets of different diameters can be made by using a narrower or wider tube, and, correspondingly, different core diameters, while pellet length can be adjusted by lowering the pin within the tube to a lesser or greater degree as molten pellet material is drawn into the tube interior.

The above-described process for making core-and-shell pellets can be adapted to make pellets with more than one shell, by using an elongated pin with multiple segments and segment-by-segment step-wise lowering of the pin within the tube, as each shell is made and allowed to harden within the pelleting tube.

Channel capping, as explained earlier in this section, facilitates pellet formation in a manner that allows the interior pellet to fuse and contract without formation of internal cavities or sinks. This is done, in part, by lowering the pin within the tube in a gradual manner, and in part by allowing a small amount of pelleting composition to remain in the funnel just above the funnel-tube junction.

In a preferred approach, channel capping is carried out in shell formation, core formation, or, more preferably, both. Following completion of pellet manufacture, the completed pellet is released using any effective method.

It should be noted that the invention is not limited with respect to the aforementioned methods of manufacture, and that other methods for making the pellet implants are possible, including modified versions of the aforementioned methods or entirely different methods known to those of ordinary skill in the art.

To scale up pellet manufacture, it will be appreciated that automation of one or more aspects of the method is desirable. For example, an automated pin positioning means would be useful for moving the elongated pin vertically into and through the pelleting tube and then withdrawing the pin, wherein the pin would be withdrawn stepwise in a core-and-shell manufacturing method such as that described above. As another example, an automated means for filling the funnel or a functionally equivalent reservoir with pelleting material, including shell material and core material, would be desirable, as would a reservoir cleaning technique and a pellet removal system. Other such automated means will be apparent to those of ordinary skill in the art and/or are described in the pertinent texts and literature.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

EXPERIMENTAL

General Procedure A—Monolithic Pellet Manufacture:

Subdermally implantable monolithic pellets of the invention were prepared in these examples using a hot melt method, as described below.

System preparation: A funnel as illustrated in the hot melt molding system of FIGS. 2A and 2B was heated to a temperature just high enough to render the pellet composition flowable. A length of PTFE tubing, cut to allow a seal to form between the heated funnel and the tubing, was placed into a heated collar to bring the temperature to just below the transition temperature of the powder, i.e., the temperature at which the powder transforms from a substantially solid form into a flowable form. The collar, with PTFE tube attached, was placed on a drawing pin such that the pin extended through the length of the tube, terminating just below the funnel. The pin is sized such that its diameter is sufficiently close to the inner diameter of the PTFE tube to provide a sealing fit therebetween. The funnel was then brought into contact with the top of the heated collar and therefore with the pin as well, such that the channel's opening was aligned with the center of the pin, collar and tube. This arrangement created a seal between the channel's opening and the upper region of the PTFE tubing.

Materials: cholesterol; phosphatidylcholine or lecithin; and etonogestrel.

Monolithic pellet preparation: All materials were fully dissolved in ethanol, and the ethanol was then evaporated to leave a homogeneous composition of the pellet components as a powder. These materials may, alternatively, be slurried by hand or machine mixing in any USP grade organic solvent, with ethanol preferred. In formulations with free-flowing dry powders, dry-mixing equipment, such as V-blenders or other type of blenders, may be used.

The powdery pellet composition was poured directly into the heated funnel. The amount of material added to the funnel was calculated to provide enough material to fill the PTFE tubing cavity as well as create a residual in the funnel that capped off the PTFE tubing, thereby causing a complete fill of the cavity and preventing air from entering and creating voids and cracks in the pellet. As the powdered material reached its transition temperature and became flowable, the pin was lowered through the PTFE tubing, drawing the pellet composition into the tube and forming an elongated rod.

Pellet post processing: The rod was allowed to cool in ambient conditions in place for approximately 30 to 60 seconds prior to removing the collar and PTFE tube for cooling at room temperature. Once the rod cooled, it was ejected from the PTFE tube with a pin and inspected. It was then available for trimming to predetermined pellet dimensions using a hot knife.

General Procedure B—Manufacture of Core-and-Shell Pellets, Drug-Containing Core ("Core-Type Pellets"):

Modifications were made to the above procedure for making monolithic pellets in order to make core-and-shell pellets, i.e., subdermally implantable pellets with a drug-containing core in an inert shell. The pellet manufacturing assembly used to make core-and-shell pellets is schematically illustrated in FIGS. 3A through 3E.

System preparation: The hot melt molding system was set up and readied for pellet manufacture as described above with respect to monolithic pellets.

Materials for the drug-containing core: cholesterol; phosphatidylcholine and/or lecithin; and etonogestrel.

Materials for the inert shell: lipid only, e.g., cholesterol and/or phosphatidylcholine.

Preparation: All core materials were fully dissolved in ethanol, and the ethanol was then evaporated to leave a homogeneous composition of the core components as a powder. Shell materials were slurried in ethanol, and the ethanol was then evaporated to leave a homogeneous composition of the shell components as a powder.

In this case, in contrast to monolith manufacture, as described in General Procedure A, a double pin was used to fabricate the core-and-shell pellet in two stages. The double pin was made by assembling a narrower pin on top of and in axial alignment with the somewhat wider pin used for monolith preparation, the narrower pin forming an extended narrower segment of an integral pin structure.

The powdery shell composition was poured directly into the heated funnel. The amount of material added to the funnel was calculated to provide enough material to fill the PTFE tubing cavity, with the narrower pin segment container therein, and create a residual in the funnel that capped off the PTFE tubing. This resulted in complete filling the cavity and preventing air from entering and creating voids and cracks in the shell. As the powdered material in the heated funnel began to coalesce and flow, the pin was lowered through the PTFE tubing, drawing the flowable shell material, along with the extended narrower segment of the pin, into the tube and forming an elongated cylinder around the narrower pin segment. The cylinder thus formed was composed of the shell composition and serves as the shell of the final pellet. To form the core, the funnel was wiped clean of shell material and the mixed core powder was then added into the funnel. After heating the core composition until flowable, the pin was drawn down a second time, so that the narrower upper segment was withdrawn almost completely from the solidified shell. The tight contact between the shell and pin, and between the tube and funnel, resulted in a partial vacuum as the pin is withdrawn from the shell, thereby siphoning flowable core material from the funnel into the shell. The core was allowed to cool and harden within the shell. The tube was then removed from the apparatus and the core-and-shell pellet allowed to further cool at room temperature before being extracted from the tube.

General Procedure C—Manufacture of Core-and-Shell Pellets, Drug-Containing Shell ("Shell-Type Pellets"):

Core-and-shell pellets with a drug-containing shell and an inert core (i.e., "shell-type pellets) were manufactured using the process of General Procedure B, except that the drug-containing material was added to the funnel first to form the shell, and the inert material added second to form the core.

Unless otherwise indicated, all percentages herein are weight % (wt. %), all ratios are weight ratios, and all width and length measurements are in millimeters.

Example 1

Monolithic Pellets: Effect of Pellet Diameter on Release Rate and Duration

Rod-shaped, substantially cylindrical monolithic pellets, having identical compositions but differing in diameter, were made using General Procedure A.

Composition: 85 wt. % etonogestrel ("ENG"), 3 wt. % phosphatidylcholine ("PC"), and 12 wt. % cholesterol ("CH").

The pellets made were both 4 mm in length, with one pellet having a diameter of 1.7 mm (a "monolithic thin" type of pellet) and the other pellet having a diameter of 2.8 mm (a "monolithic thick" type of pellet). Drug release rate in 95.0% denatured ethanol (i.e., anhydrous ethanol denatured with 5 vol. % methanol and 5 vol. % isopropanol) and 5% deionized water was evaluated over a time period of about 30 minutes, as follows:

50.0 ml of the 95.0% ethanol dissolution medium were added to a 125 mL Erlenmeyer flask, which was then sealed with paraffin film. Two capillary tubes were inserted through the film and into the dissolution medium, and were connected to a peristaltic pump that circulated the solution at 4 mL/min through a 0.2 mm path length quartz cuvette in a UV-Vis spectrometer. The pellet was dropped into the dissolution medium, which was stirred at room temperature in the flask on an orbital shaker set to 150 rpm. The absorbance was measured at 240 nm, as ENG absorbs strongly at that wavelength while the excipients, CH and PC, do not. Absorbance measurements were taken at 1-second intervals for 15 to 180 minutes until the spectrometer response remained constant, indicating complete dissolution of the pellet.

Figure 4:
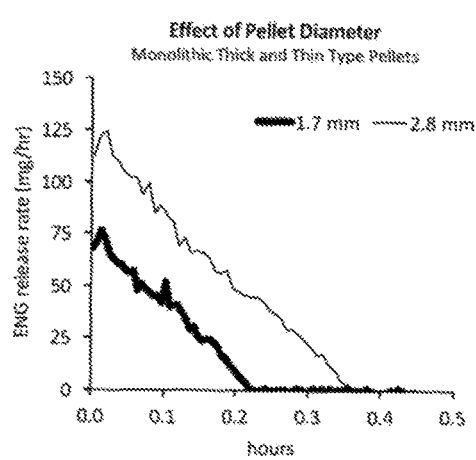
FIG. 4 provides the dissolution profiles for monolithic pellet implants with different diameters, as described in Example 1.

The dissolution profiles are shown in FIG. 4. The thinner monolithic pellets clearly stopped ENG release much earlier than thicker, more traditional pellets, and they also started with a lower dose. As may be seen in the figure, increasing the pellet diameter increased both duration of drug release, i.e., the time period during which a measurable drug concentration was seen, and the drug release rate.

Example 2

Monolithic Pellets: Effect of Pellet Length on Release Rate and Release Duration Two groups of rod-shaped, substantially cylindrical monolithic pellets, having identical compositions but differing in length, were made using General Procedure A.

Composition: 85 wt. % ENG, 3 wt. % PC, and 12 wt. % CH.

Figure 5:
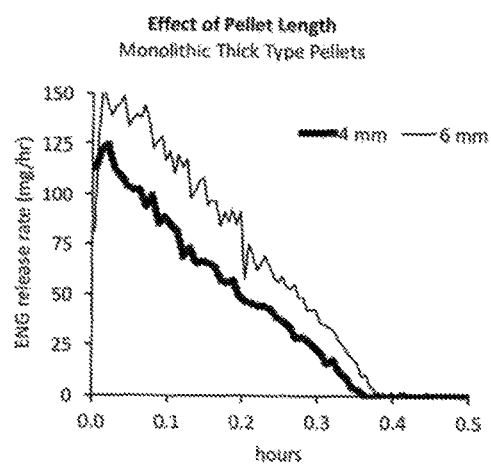
FIG. 5 provides the dissolution profiles for monolithic pellet implants with different lengths, as described in Example 2.

The pellets made were both 2.8 mm in diameter, with one pellet having a length of 4 mm and another pellet having a length of 6 mm. The dissolution profiles obtained using the methodology described in Example 1 are shown in FIG. 5. As may be seen in the figure, the two pellets released drug over a time period of similar duration, but the shorter pellets gave rise to a shallower slope for the decreasing rate of etonogestrel release, meaning that the release rate for the longer pellets decreased faster than that of the shorter pellets.

Example 3

Core-Type Pellets: Release Rate and Duration

General Procedure B was followed to prepare pellets having a core of 85 wt. % ENG, 12 wt. % CH, and 3 wt. % PC, and a shell of 97 wt. % CH and 3 wt. % PC. The diameter of each core was 1.6 mm and each shell was 0.6 mm thick, giving a total pellet diameter of 2.8 mm. Pellet length was 4 mm. Drug release over time was evaluated in 95% ethanol as described in Example 1. Results are shown in the dissolution profile of FIG. 6 (see the curve corresponding to the pellet length of 4 mm).

Example 4

Core-Type Pellets: Effect of Pellet Length on Release Rate and Duration

Figure 6:
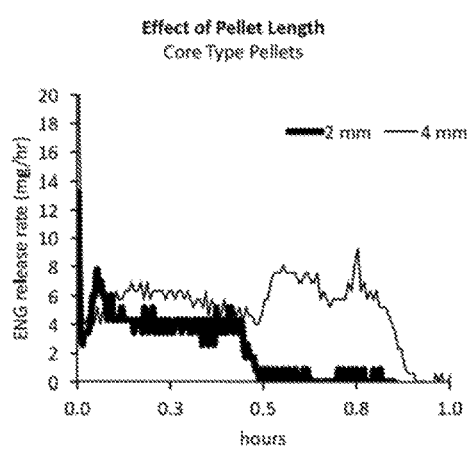
FIG. 6 provides the dissolution profile for core-type pellets, as described in Examples 3 and 4.

General Procedure B was followed to prepare core-type pellets having a core of 85 wt. % ENG, 12 wt. % CH, and 3 wt. % PC, and a shell of CH and PC in a 97:3 weight ratio. For purposes of evaluating the effect of pellet length on release rate and duration with core-type pellets, a core pellet was prepared as in Example 3, but with a pellet length of 2 mm. Drug release rate was evaluated as described in Example 1, and the dissolution profiles are shown in FIG. 6. Comparing the figure with the release profiles of the monolithic pellets shows that the ENG release rate is significantly slower with core-type pellets than with monolithic pellets. Doubling the core pellet length from 2 mm to 4 mm doubled the ENG release duration while maintaining a fairly even ENG release rate of approximately 5 mg/hr.

Example 5

Shell-Type Pellets: Effect of Pellet Length on Release Rate and Duration

Figure 7:
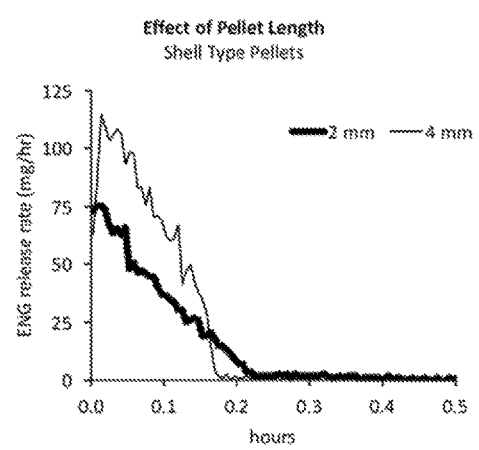
FIG. 7 provides the dissolution profiles for shell-type pellets of different lengths, as described in Example 5.

General Procedure C was followed to prepare shell-type pellets having a core of CH and PC in a 97:3 weight ratio and a shell of 85 wt. % ENG, 12 wt. % CH, and 3 wt. % PC. The diameter of each core was 1.6 mm and each shell was 0.6 mm thick. As in the preceding example, a first pellet was prepared that was 2 mm in length, and a second pellet was prepared that was 4 mm in length. Drug release rate in ethanol was evaluated as described in Example 1. The dissolution profiles for the two pellet groups are shown in FIG. 7. In this case, increasing the length of the pellet did not substantially change the duration of ENG release, but did increase ENG release rate. Shell pellets are designed to have a rapid cessation of ENG release once the shell has eroded to the CH core. This can be seen with the 4 mm shell pellet, compared to the 4 mm monolithic pellet, but was not clearly seen in the 2 mm shell pellet.

Figure 8A:
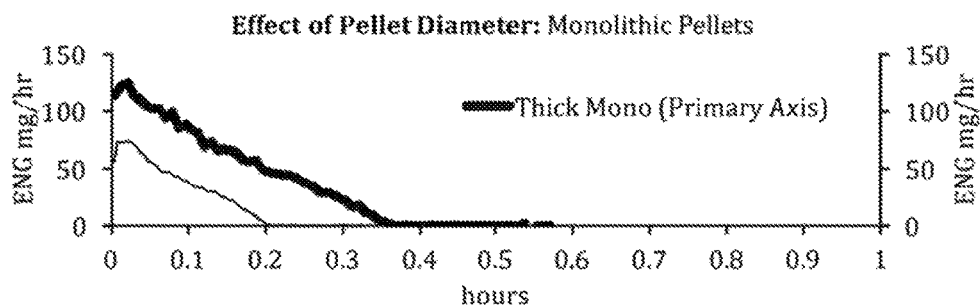
FIG. 8A shows the dissolution profiles of thin monolithic pellets compared with thick monolithic pellets, as also described in Example 5.
Figure 8B:
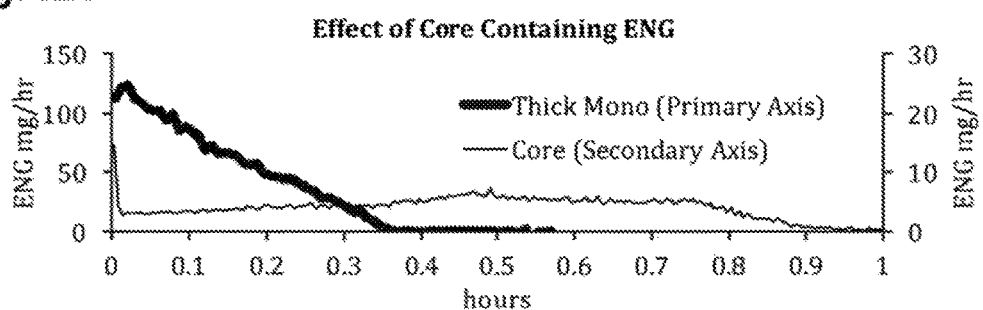
FIG. 8B shows the dissolution profiles of core-type pellets compared with thick monolithic pellets, as also described in Example 5.
Figure 8C:
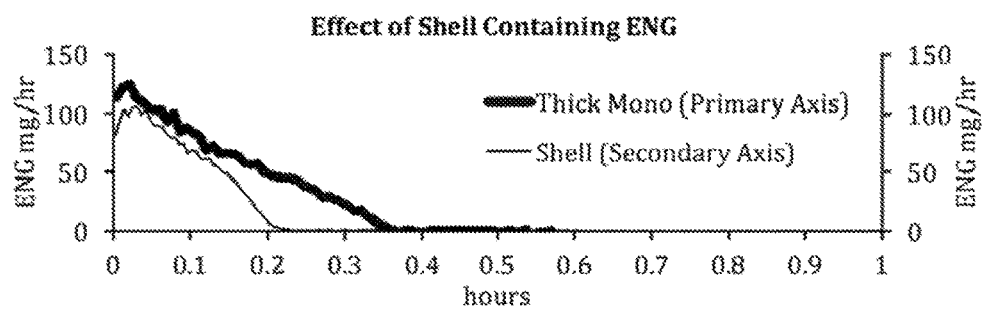
FIG. 8C shows the dissolution profiles of shell-type pellets compared with thick monolithic pellets, as also described in Example 5.
Figure 9:
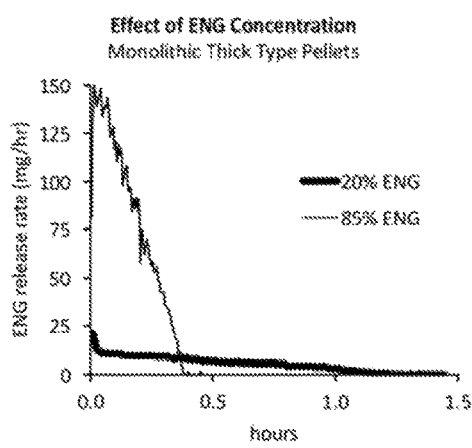
FIGS. 9 through 12 illustrate the effect of active agent concentration on release rate, in thick monolithic pellets (FIG. 9), thin monolithic pellets (FIG. 10), core-type pellets (FIG. 11), and shell-type pellets (FIG. 12), as described in Example 6.
Figure 10:
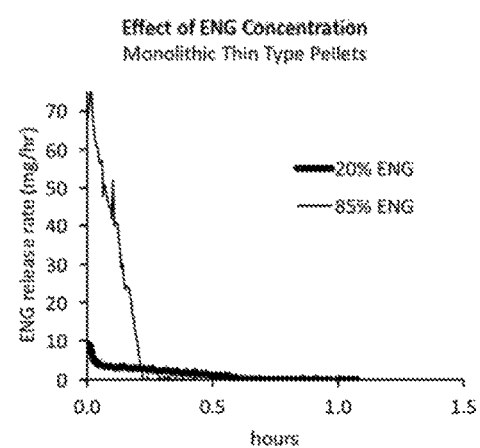
Figure 11:
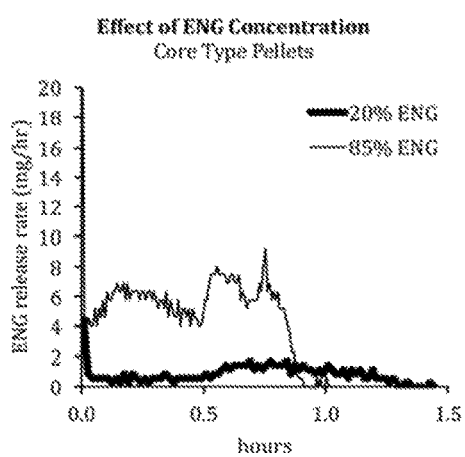
Figure 12:
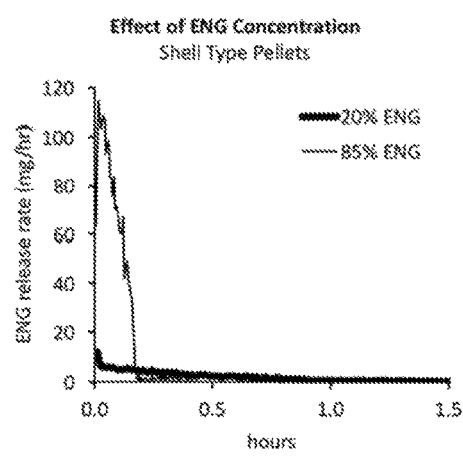
Figure 13:
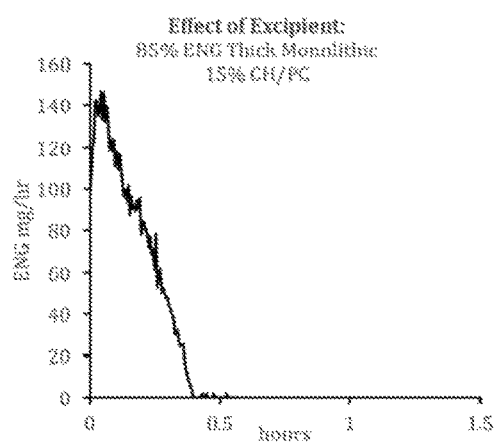
FIGS. 13 through 17 illustrate the effect of excipient selection on release rate, as described in Example 7.
Figure 14:
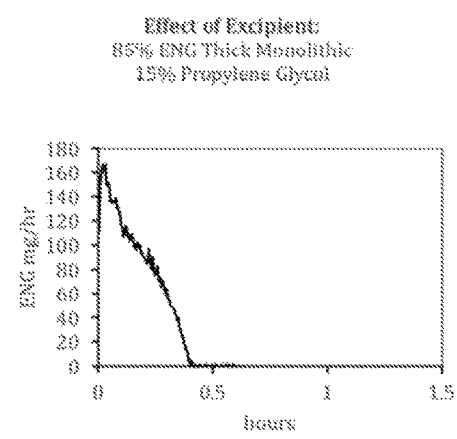
Figure 15:
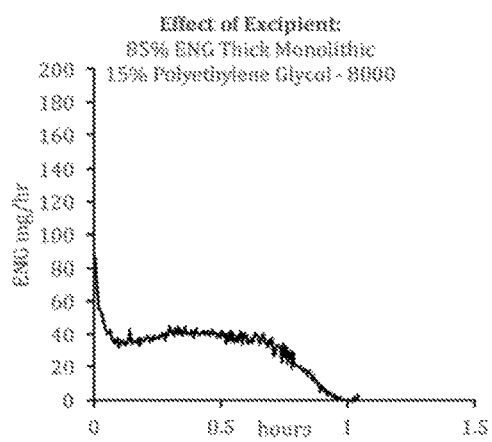
Figure 16:
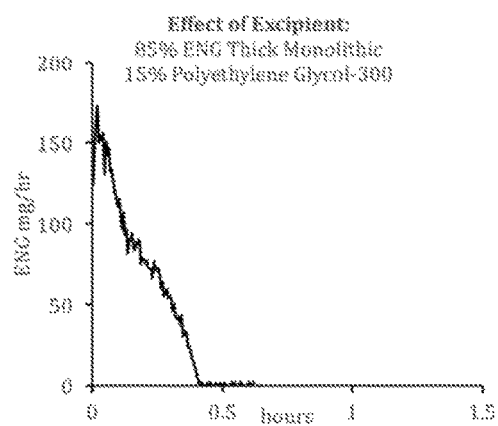
Figure 17:
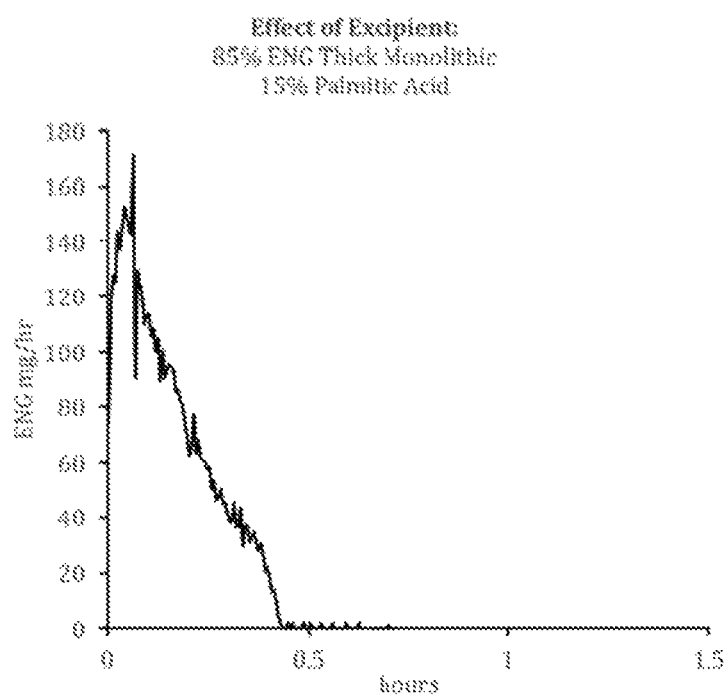

For purposes of comparison, the dissolution profiles obtained for the thick monolithic pellets and thin monolithic pellets (Example 1) are shown as a group in FIG. 8A, with the dissolution profiles obtained for core-type pellets (Example 3) and shell-type pellets (Example 5), all pellets 4 mm in length, shown in FIGS. 8B and 8C, respectively.

Example 6

Effect of Drug Concentration on Drug Release Profile

In order to assess the concentration of drug in the implant on the drug release profile, four types of pellets were made, with two drug concentration subgroups prepared for each of the four pellet types:

Type (I), Monolithic thick pellets. Dimensions: Diameter, 2.8 mm, length, 6 mm. Type (I), subgroup (A): 85% ENG, 12% CH, 3% PC. Type (I), subgroup (B): 20% ENG, 77% CH, 3% PC.

Type (II), Monolithic thin pellets. Dimensions: Diameter, 1.7 mm; length, 4 mm. -Type (II), subgroup (A): 85% ENG, 12% CH, 3% PC. Type (II), subgroup (B): 20% ENG, 77% CH, 3% PC.

Type (III), Core-type pellets. Dimensions: Core diameter, 1.6 mm; shell thickness, 0.6 mm; length, 4 mm. Type (III), subgroup (A): 85% ENG, 12% CH, 3% PC core and 97% CH, 3% PC shell. Type (III), subgroup (B): 20% ENG, 77% CH, 3% PC core and 97% CH, 3% PC shell.

Type (IV), Shell-type pellets. Dimensions: Core diameter, 1.6 mm; shell thickness, 0.6 mm; length, 4 mm. Type (IV), subgroup (A): 85% ENG, 12% CH, 3% PC shell and 97% CH, 3% PC core. Type (IV), subgroup (B): 20% ENG, 77% CH, 3% PC shell and 97% CH, 3% PC core.

The release rate results obtained using the method of Example 1 can be seen in the comparative release profiles of FIGS. 9 through 12. With all four pellet types, thick, thin, core and shell, the rate of ENG release increased with an increase in ENG content, while the release duration decreased with an increase in ENG content. While the approximately four-fold greater ENG content in the 85% ENG pellets relative to the 20% ENG pellets might have been expected to give an approximately four-fold greater release rate of ENG, the EN release from the 85% pellets was, surprisingly, substantially higher than four-fold faster. ENG release from pellets with higher CH content is slowed because the aqueous solubility of a 20% ENG/80% CH solid mixture is lower than one containing 85% ENG/15% CH.

Example 7

Effect of Changing Excipient on Drug Release Profile

In order to assess the impact of a change in excipient on drug release profile from pellet implants, several monolithic pellets were made with different excipient compositions but were otherwise identical. Pellet dimensions: diameter 2.8 mm, length 6 mm. Composition: 85% ENG, 15% excipient. Pellets were made with the excipients indicated below:

Excipient 1: CH/PC at a 4:1 weight ratio.
Excipient 2: Propylene glycol (PG).
Excipient 3: Polyethylene glycol 8000 (PEG-8000).
Excipient 4: Polyethylene glycol 300 (PEG-300).
Excipient 5: Palmitic acid (PA).

Dissolution profiles obtained using the method of Example 1 are provided in FIGS. 13 through 17 for Excipients 1 through 5, respectively.

At 85% ENG, this major component, i.e., the active agent, controlled the overall release profile when relatively small molecules were used as the excipient. The addition of a large polymeric molecule, PEG-8000, was found to inhibit ENG release and increase the release duration.

Example 8

In Vivo Evaluation

Five types of pellets were prepared using the procedures of the earlier examples:

ENG thick monolithic (85% ENG, 12% CH, and 3% PC; diameter 2.8 mm, length 6 mm;

ENG thin monolithic (85% ENG, 12% CH, and 3% PC; diameter 1.7 mm, length 4 mm;

ENG shell (core of CH/PG at a 97:3 ratio; shell of 85% ENG, 12% CH, and 3% PG; core diameter 1.6 mm, shell thickness 0.6 mm, and length 4 mm;

ENG core (core of 85% ENG, 12% CH, and 3% PG; shell of CH/PC at a 97:3 weight ratio; core diameter 1.6 mm, shell thickness 0.6 mm, and length 4 mm; and NET (norethindrone) thick monolithic (85% NET, 15% CH); diameter 2.8 mm, length 6 mm.

Figure 18:
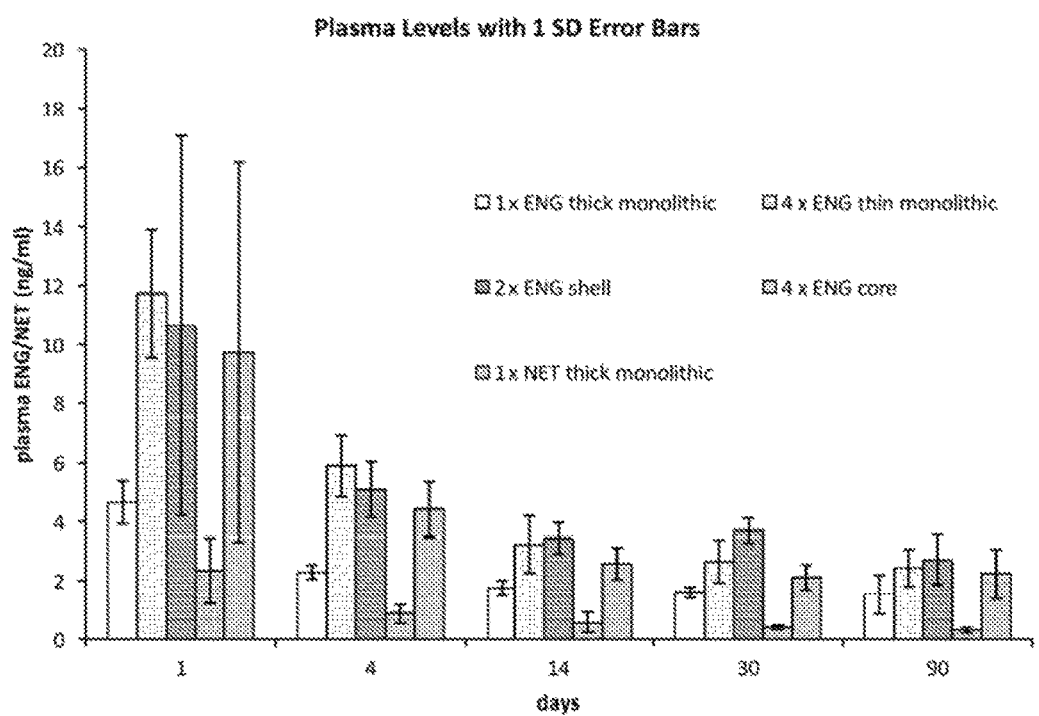
FIG. 18 illustrates the in vivo test results obtained in Example 8, showing plasma progestin levels measured at different post-implantation time points.

The five pellet types were implanted subcutaneously into eight rats per pellet type (except for NET thick monolithic, where pellet one was pulled out by the animal sometime during day 1). The number of pellets implanted per rat was chosen to keep the total ENG doses similar (32±5 mg). Pellets were implanted separately on the animal's back. Rats received a 1×ENG or NET thick monolithic pellet above one front leg, or 2× shell pellets above both front legs, or 4× thin monolithic pellets or core pellets above all four legs. Blood plasma levels were evaluated at day 1, day 4, day 14, day 30, and day 90. Extended release was achieved with all pellets, as indicated by FIG. 18.

Figure 19:
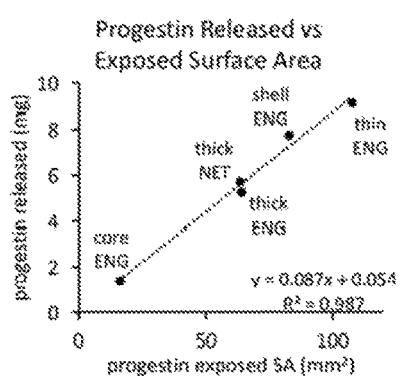
FIG. 19 shows the correlation between total drug released and the exposed surface area of drug-containing regions within the pellet, as determined in Example 8, while FIG. 20 provides the AUC (mg*day/mL) versus amount of drug released.
Figure 20:
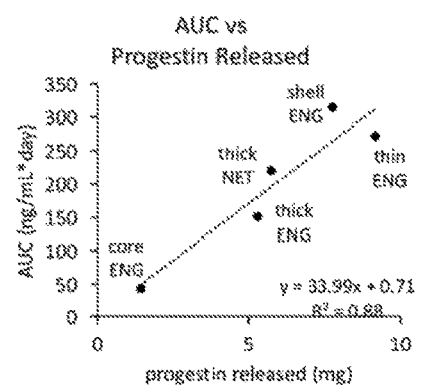

Then, the unreleased progestin per rat was averaged for each pellet type, and the amount released was calculated by difference from the average starting content based on the analysis of pellets made in the same batches as those implanted. FIG. 19 shows that the amount of progestin initially released from the pellets tightly correlates with the exposed surface area, supporting the same surface erosion mechanism in vivo as that seen in vitro, and also supporting a correlation between ENG loss and blood levels, implying that the amount of drug released and the rate of drug release can be controlled by varying exposed ENG surface area. A good correlation showing a linear dose response was found between the blood concentration integrated over the three-month exposure (i.e., the area under the curve or "AUC") and the amount of progestin released from the pellets, as seen in FIG. 20.

We claim:

1. A drug delivery system for use in female contraception, comprising a subdermally implantable, bioerodible, monolithic pellet that provides for controlled release of a contraceptive agent throughout an extended drug delivery time period that ends with complete bioerosion of the pellet in situ, the pellet being substantially homogeneous, lipophilic, and substantially cylindrical with a length-to-width ratio greater than about 5:1, and having a density in the range of about 0.75 g/cm³ to about 1.25 g/cm³, the pellet comprising the contraceptive agent, a first excipient having a first aqueous solubility, and a second excipient having a second aqueous solubility that is at least 10% greater than the first aqueous solubility, wherein the weight ratio of the first excipient to the second excipient is in the range of about 2:1 to about 100:1, and further wherein the contraceptive agent is present in an amount that, following subdermal implantation of at least one pellet into a female subject, results in a serum level of the contraceptive agent sufficient to achieve contraceptive efficacy during the extended drug delivery time period, wherein the extended drug delivery time period comprises an effective drug delivery time period in the range of about six months to about four years during which the active agent is released at a dosage sufficient to provide contraceptive efficacy.

2. The drug delivery system of claim 1, comprising two to six pellets.

3. The drug delivery system of claim 1, wherein any hydrophilic components in the pellet represent less than about 35 wt. % of the pellet.

4. The drug delivery system of claim 1, wherein the pellet comprises a solid at temperatures in the range of about 35° C. to about 40° C.

5. The drug delivery system of claim 1, wherein any inactive components contained within the pellet are bioresorbable and/or water soluble, or are transformed in situ during pellet bioerosion into at least one bioresorbable and/or water-soluble species.

6. The drug delivery system of claim 1, wherein the contraceptive agent comprises a progestogen.

7. The drug delivery system of claim 6, wherein the progestogen is selected from 21-acetoxypregnenolone, allylestrenol, anagestone, chlormadinone, chloroethynyl norgestrel, cyproterone, desogestrel, dienogest, dimethisterone, drospirenone, ethisterone, ethynerone, etynodiol, etonogestrel, gestodene, hydroxyprogesterone, levonorgestrel, lynestrenol, medrogestone, medroxyprogesterone, megestrol, nomegestrol, norethindrone, norelgestromin, noretynodrel, norgestimate, norgestrel, norgestrienone, progesterone, retroprogesterone, and combinations of any of the foregoing.

8. The drug delivery system of claim 7, wherein the progestogen is etonogestrel.

9. The drug delivery system of claim 7, wherein the progestogen is levonorgestrel.

10. The drug delivery system of claim 6, wherein the contraceptive agent further comprises an estrogenic compound.

11. The drug delivery system of claim 1, wherein the pellet has a pharmacokinetic profile determined by at least one pellet property selected from width, length, diameter, surface area, size, composition, hardness, and degree of crystallinity.

12. The drug delivery system of claim 1, wherein the pellet comprises a composition that is flowable at a selected temperature in the range of about 50° C. to about 250° C.

13. A method for administering a contraceptive agent to a female individual in a sustained release manner over an extended drug delivery time period, comprising subdermally implanting the drug delivery system of claim 1 into the individual and allowing the drug delivery system to remain in place throughout the extended drug delivery time period.

14. The drug delivery system of claim 1, wherein the effective drug delivery time period is in the range of about one year to about three years.

15. A delivery system for use in female contraception, comprising a subdermally implantable-bioerodible, lipophilic pellet that provides for controlled release of a progestogen throughout an extended drug delivery time period that ends with complete bioerosion of the pellet in situ, the pellet comprising:
an amount of a progestogen selected from etonogestrel and levonorgestrel, which, following subdermal implantation of at least one pellet into a female subject, results in a serum level of the progestogen sufficient to achieve contraceptive efficacy during an effective drug delivery time period of about six months to about four years within the extended drug delivery time period; and
an excipient composition comprising (a) a first lipidic excipient having a first aqueous solubility and a second lipidic excipient having a second aqueous solubility, where the first aqueous solubility is lower than the second aqueous solubility by at least 10% and the weight ratio of the first lipidic excipient to the second lipidic excipient is in the range of about 3:1 to about 50:1.

16. The drug delivery system of claim 15, wherein the first lipidic excipient comprises a sterol, a sterol ester, or a mixture of a sterol and a sterol ester, and the second lipidic excipient comprises a phospholipid, a glycerophospholipid, or a mixture of a phospholipid and a glycerophospholipid.

17. A method for administering a contraceptive agent to a female individual in a sustained release manner over an extended drug delivery time period, comprising subdermally implanting the drug delivery system of claim 15 into the individual and allowing the drug delivery system to remain in place throughout the extended drug delivery time period.

18. A method for administering a contraceptive agent to a female individual in a sustained release manner over an extended drug delivery time period, comprising subdermally implanting the drug delivery system of claim 16 into the individual and allowing the drug delivery system to remain in place throughout the extended drug delivery time period.

19. The drug delivery system of claim 1, wherein the weight ratio of the first lipidic excipient to the second lipidic excipient is in the range of about 3:1 to about 50:1.

20. The drug delivery system of claim 19, wherein the weight ratio of the first lipidic excipient to the second lipidic excipient is in the range of about 3.5:1 to about 25:1.

21. The drug delivery system of claim 1, wherein the pellet has a density in the range of about 0.90 g/cm$^3$ to about 1.10 g/cm$^3$.

22. The drug delivery system of claim 21, wherein the pellet has a density in the range of about 0.95 g/cm$^3$ to about 1.05 g/cm$^3$.

23. The drug delivery system of claim 1, wherein the contraceptive agent represents about 75 wt. % to about 95 wt. % of the pellet.

24. A drug delivery system for use in female contraception, comprising a subdermally implantable, bioerodible, monolithic pellet that provides for controlled release of a contraceptive agent throughout an extended drug delivery time period that ends with complete bioerosion of the pellet in situ, the pellet being substantially homogeneous, lipophilic, and substantially cylindrical with a length-to-width ratio of greater than about 5:1, having a density in the range of about 0.95 g/cm$^3$ to about 1.05 g/cm$^3$, and comprising about 75 wt. % to about 95 wt. % contraceptive agent, a first excipient having a first aqueous solubility, and a second excipient having a second aqueous solubility that is at least 10% greater than the first aqueous solubility, wherein the weight ratio of the first excipient to the second excipient is in the range of about 3.5:1 to about 25:1, and further wherein the contraceptive agent is present in an amount that, following subdermal implantation of at least one pellet into a female subject, results in a serum level of the contraceptive agent sufficient to achieve contraceptive efficacy during the extended drug delivery time period, wherein the extended drug delivery time period comprises an effective drug delivery time period in the range of about six months to about four years during which the active agent is released at a dosage sufficient to provide contraceptive efficacy.

* * * * *